United States Patent
Foster et al.

(10) Patent No.: US 10,487,362 B2
(45) Date of Patent: Nov. 26, 2019

(54) METHODS FOR DIAGNOSING CANCER BASED ON SMALL NUCLEOLAR RNA HBII-52

(71) Applicant: Health Research, Inc., Buffalo, NY (US)

(72) Inventors: Barbara Foster, Buffalo, NY (US); Steven J. Seedhouse, East Amherst, NY (US); Jason Kirk, Getzville, NY (US)

(73) Assignee: Health Research, Inc., Buffalo, NY (US)

( * ) Notice: Subject to any disclaimer, the term of this patent is extended or adjusted under 35 U.S.C. 154(b) by 689 days.

(21) Appl. No.: 14/759,696

(22) PCT Filed: Jan. 9, 2014

(86) PCT No.: PCT/US2014/010827
§ 371 (c)(1),
(2) Date: Jul. 8, 2015

(87) PCT Pub. No.: WO2014/110230
PCT Pub. Date: Jul. 17, 2014

(65) Prior Publication Data
US 2015/0354011 A1    Dec. 10, 2015

Related U.S. Application Data

(60) Provisional application No. 61/750,554, filed on Jan. 9, 2013.

(51) Int. Cl.
*C12Q 1/68* (2018.01)
*C12Q 1/6886* (2018.01)
*A61K 31/444* (2006.01)

(52) U.S. Cl.
CPC .......... *C12Q 1/6886* (2013.01); *A61K 31/444* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,945,847 B2 * | 2/2015 | Benvenisty | G01N 33/5014 435/32 |
| 2007/0077578 A1 | 4/2007 | Penning et al. | |
| 2010/0150930 A1 | 6/2010 | Wilson et al. | |
| 2014/0296085 A1 * | 10/2014 | Baker | G01N 33/57415 506/8 |

FOREIGN PATENT DOCUMENTS

| | | |
|---|---|---|
| WO | 2004/070056 A2 | 8/2004 |
| WO | 2012/009667 A2 | 1/2012 |

OTHER PUBLICATIONS

Crea et al. (Cancer Metastasis Rev, 2014, 33:1-16).*
Lowe et al. (Nucleic Acids Research, 1990, 18(7):1757-1761).*
Mannoor et al. (Biochim Biophys Acta, 2012, 1826(1):121-128).*
Dong et al. (Hum Molec Genet 2008, 17(7):1031-1042) (Year: 2008).*
Marteaux et al. (Serotonin: Biosynthesis, Regulation, and Health Implications; Ed: Scott Hall, 2012, p. 1-28) (Year: 2012).*
Mannoor, K. et al., Small Nucleolar RNAs in Cancer, Biochimica et Biophysica Acta, Apr. 2, 2012, vol. 1826, pp. 121-128.

* cited by examiner

*Primary Examiner* — Stephanie K Mummert
(74) *Attorney, Agent, or Firm* — Hodgson Russ LLP

(57) ABSTRACT

Provided are compositions and methods for detecting in a sample the presence or absence, and/or the amount, of a small nucleolar RNA (snoRNA) HBII-52, also known as SNORD115. The compositions and methods are useful in diagnosis, prognosis, therapy recommendations, therapy, and monitoring of therapy for individuals who have a disorder that is positively correlated with elevated HBII-52, such as cancer, and particularly for prostate cancer. Kits containing primers for detecting and/or amplifying HBII-52 from a biological sample are provided. The disclosure includes a method for monitoring an individual undergoing therapy for a disorder associated with HBII-52 expression, a method for identifying an individual as a candidate for therapy with an antagonist of $5\text{-HT}_{2c}\text{R}$, and a method for therapy by administering to a subject a therapeutically effective amount of an antagonist of $5\text{-HT}_{2c}\text{R}$.

9 Claims, 26 Drawing Sheets

Specification includes a Sequence Listing.

1 – C2D MBII52

2 – C2D Scramble

3 – C2G MBII52

4 – C2G Scramble

5 – No RT Control

Figure 13

Consensus sequence

GGGTC*R*ATGATGAGAACCTTATATTGT*Y*CTGAAGAGAGGTGATGACTTAAAAATCATGCTCAATAGGATTA*Y*GCTGAGGCCC
(SEQ ID NO:1)

Individual sequences: (sequences 1-47 numbered in this Figure are SEQ ID NO:10 – SEQ ID NO:56, respectively)

```
1.  GTGTTGATGATGAGAACCTTATATTATCCTGAAGAGAGGTGATGACTTAAAAATCATGCTCAATAGGATTACGCTGAGGCCC
2.  GGGTCGATGATGAGAAGCTTCTGTTTTCTTGAAGAGAGGTGATGACTTAAAAATCATGCTCAATAGGATTATGCTGAGGCCC
3.  GGGTCAATGATGAGAACCTTATATTGTCCTGAAGAGAGGTGATGACTTAAAAATCATGCTTAGTAGGATTACGCTGAGGCCT
4.  GGGTCGATGATGAGAACTTTATATTGTTCTGAAGAGAGGTGATGACTTAAAAATCATGCTCAATAGGATTACGCTGAGGCCC
5.  GGATCGATGATGAGAACCTTATATTGTCCTGAAGAGAGGTGATGACTTAAAAATCATGCTCAATAGGATTACGCTGAGGCCC
6.  GGGTCAATGATGAGAACCTTATATTGTTCTGAAGAGAGGTGATGACTTAAAAATCATGCTCAATAGGATTACGCTGAGGCCC
7.  GGGTCAATGA___GAACCTTATATTGTCCTGAAGAGAGGTGATAACTTAAAAATCATGCTCAATA^ATA^GGATTACGCTGAGGCCC
8.  GGGTCAATGATGAGAACCTTACATTGTTCTGAAGAGAGATGATGACTTAAAAATCATGCTCAATAGGATTACGCTGAGGCCC
9.  GGGTCGATGATGAGAACCTTATATTGTCCTGAAGAGAGGTGATGACTTAAAAATCATGCTCAATAGGATTACGCTGAGGCCC
10. GGGTCGATGATGAGAACCTTATATTGT_CTGAAGAGAGGTGATGACTTAAAAATCATGCTCAATAGGATTACGCTGAGGCCC
11. GGGTCAATGATGAGAACCTTATATTGTCCTGAAGAGAGGTGATGACTTAAAAATCATGCTCAATAGGATTACGCTGAGGCCC
12. GGGTCGATGATGAGAACCTTATATTGTCCTGAAGAGAGGTGATGACTTAAAAATCATGCTCAATAGGATTACGCTGAGGCCC
13. GGGTCGATGATGAGAACCTTATATTATCCTGAAGAGAGGTGATGACTTAAAAATCATGCTCAATAGGATTACGCTGAGGCCC
14. GGGTCGATGATGAGAAACTTATATTGT_CTGAAGAGAGGTGATGACTTAAAAATCATGCTCAATAGGATTACGCTGAGGCCC
15. GGGTCGATGATGAGAACCTTATATGTT_CTGAAGAGAGGTGATGACTTAAAAATCATGCTCAATAGGATTACGCTGAGGCCC
16. GGGTCAATGATGAGAACCTTATATTATCCTGAAGAGAGGTGATGACTTAAAAATCATGCTCAATAGGATTACGCTGAGGCCC
17. GGGTCGATGATGAGAACCTTATATTGTCCTGAAGAGAGGTGATGACTTAAAAATCATTCTCAAAAGGATTATGCTGAGGCCC
18. GGGTCGATGATGAGAACCTTATATTGTCCTGAAGAGAGGTGATGACTTAAAAATCATTCTCAAAAGGATTATGCTGAGGCCC
19. GGGTCGATGATGAGAACCTTATATTGTCCTGAAGAGAGGTGATGACTTAAAAATCATTCTCAAAAGGATTATGCTGAGGCCC
20. GGGTCGATGATGAGAACCTTATATTGTCCTGAAGAGAGGTGATGACTTAAAAATCATGCTCAATAGGATTATGCTGAGGCCC
21. GGGTCGATGATGAGAACCTTATATTTT_CTGAAGAGAGGTGATGACTTAAAAATCATGCTCAATAGGATTACGCTGAGGCCC
22. GGGTCAATGATGAGAACCTTATATTGTCCTGAAGAGAGGTGATGACTTAAAAATCATGCTCAATAGGATTACGCTGAGTCCC
23. GGGTCAATGATGAGAACCCTATATTGTGTTGAAGAGAGGTGATGACTTAAAA_T^TAC^CATGCTCAATGATTACGCTGAGGCCC
24. _____GAGAACCTTATATTGTTCTGAAGAGAGGTGGTGACTTAAAAATCATGCTCAATAGGATTACGCTGAGGCCC
25. AGGTCGATTATGAGAACCTTATATTGTCCTGAAGAGAGGTGATGACTTAAAAATCATGCCCAATAGGATTACGCTGAGGCCC
26. GGGTCAGTGATGAGAACCTTATATTGTCCTGAAGAGAGGTGATGACTTAAAAATCATGCTCAATAGGATTACGCTGAGGCCC
27. _____ATGATGAGAACCTTATATTGTCCTGAAAAGAGGTGATGACTTAACAATCATGCTCAATAGGATTACATTGAAGCCC
28. _____TGATGAGAACCTTGTATTCTTCTGAAGAGAGGTGATGACTTAAAAACCATGCTCAATAGGATTACACTTAGGCCG
29. GGGTCAATGATGAGAACCTTATATTGTCCTGAAGAGAGGTGATGACTTAAAAATCATGCTCAATAGGATTACGCTGAGGCCC
30. GGGTCAATGATGAGAACCTTATATTGTTCTGAAGAGAGGTGATTATTTAAAAATCATGCTCAATAGGATTACGCTGAGGCCC
31. GGGTCAGTGATGAGAACCTTATATTGTCCTGAAGAAAGGTGATGACTTAAAAATCATGCTCAATAGGATTACACTGAGGCCC
32. GGGTCAATGATGAGAACCTGATATTGCCCTGAAGAGAGATGATGACTTAAAAATCATGTTCAATAGGATTACGCTGAGGCCT
33. GGGTCAATGATGAGAACCGTATATTGTCCTGAAGAGCGGTGATGACTTAAAAATAATGCTCAATAGGATTACGCTGAGGCCC
34. GGGTCAATGATGAGAACCTTATAATGTTCTGAAGAGAGGTGATGACTTAAAAATCATGCTCAATAGGATTACGCTGAGGCCC
35. GGGTCAATGATGAGAACCTTGTATTATCTTGAAGAGAGGTGATGACTTAAAAATCATGCTCAATAGGATTACACTGAGGCCC
36. GGGTCAATGATGAGAACCTTATATTGTCCTGAAGAGAGGTGATGACTTAAAAATCATGCTCAATAGGATTACGCTGAGGCCC
37. GGGCTGATGATGAGAACCTTATATTGTCCTGAAAAAGGTGATGACTTAAACATCATGCTTAATAGTATTATGCTGAAGCCC
38. GGGTCAATGATGAGAACCTTACATTGTCCTGAAGAGAGATGATGACTTAAAAATCATGCTCAATAGGATTACGCTGAGGCCC
39. GGGTCAATGATGAGAATCTTATATTGTCCTGAAGAGAGGTGATGACTTAAAAATCATGCTCAATAGGATTACGCTGAGGCCC
40. GGGTCGATGATGAGAACCTTATATTTTCCTGAAGAGAGGTGATGACTTAAAAATCATGCTCAATAGGATTACGCTGAGGCCC
41. GGGTCAGTGATGAGAACCTTCTATTGTCCTGAAGAGAGGTGATGACTTAAAAATCATGCTCAATAGGATTACGCTGAGGCCC
42. GGGTCGATGATGAGAACCTTATATTGTTCTGAAGAGAGGTGATGACTTAAAAATCATGCTCAATAGGATTACGCTGAGGCCC
43. GGGTCAATGATGAGAACCTTATATTGTCCTGAAGAGAGGTGATGACTTAAAAATCATGCTCAATAGGATTACGCTGAGGCCC
44. GGGTCAATGATGAGAACCTTATATTGTCCTGAAGAGCGGTGATGACTTAAAAATCATGCTCAATAGGATTACGCTGAGGCCC
45. _____TTATATTGTCTTCGACAGGGAAGATGACATAAAAATTATGTTCAATAGGATTA_____
46. _____GTAAAAATCATGCTCAATAGAATTAAGCTGAGGCT_
47. GGGTCAATGATGAGA_TGTTA_____CTTGAAGAGAAATGATGACGTAAAAATTAAGTTCAGTTGGATTACGCTGAGGCCC
```

HBII-52 fwd: 5'-ATGAGAACCTTATATTGTCCTGAAG (SEQ ID NO:3)
HBII-52 rev: 5'-GGCCTCAGCGTAATCCTA (SEQ ID NO:4)
HBII-52 probe: 5'-/56-FAM/ GGTGATGACTTAAAAATCATGCTCAA/36-TAMSp/ (SEQ ID NO:5)
HBII-52
Slope (m) = -3.10
Efficiency (E) = $(10^{-1/m} - 1) \times 100 = 110\%$ EXAMPLE AMPLIFICATION PRODUCT (One strand)- SIZE: 73

1 - 5'- ATGAGAACCTTATATTGTCCTGAAGAGAGGTGATGACTTAAAAATCATGCT CAATAGGATTACGCTGAGGCCC – 3'
(SEQ ID NO:6)

Figure 19

All tissue

| Clinical Variable | N |
|---|---|
| Tissue type | |
| Cancer | 40 |
| Normal control tissue | 19 |

| Clinical Variable | N |
|---|---|
| Race | |
| White | 18 |
| Black | 0 |
| Other | 1 |
| Ethnicity | |
| Non-Spanish; non-Hispanic | 19 |
| Tobacco History | |
| Current user | 6 |
| Previous user | 10 |
| Never used | 3 |

Prostate cancer tissue

| Clinical Variable | N |
|---|---|
| Race | |
| White | 35 |
| Black | 4 |
| Asian | 1 |
| Ethnicity | |
| Non-spanish | 39 |
| Spanish | 1 |
| Age at Surgery (48.21 to 73.70 yrs, mean = 60.41 yrs) | |
| <60 | 17 |
| >60 | 23 |
| Smoking history | |
| Current user | 5 |
| Previous user | 10 |
| Never used | 20 |
| Unknown | 5 |

| Clinical Variable | N |
|---|---|
| Histology | |
| Adenocarcinoma | 39 |
| Combined adenocarcinoma/SCC | 1 |
| Pathological Gleason | |
| 3+3 | 20 |
| 3+5 | 1 |
| 4+3 | 1 |
| 4+4 | 5 |
| 4+5 | 10 |
| 5+4 | 3 |
| Pathological Tumor Stage | |
| 2 | 23 |
| 3 | 14 |
| 4 | 3 |

| Clinical Variable | N |
|---|---|
| Pre-RP PSA (2.9 to 87 ng/mL, mean = 8.1 ng/mL) | |
| < or = 4 | 14 |
| >4 | 26 |
| Biochemical Failure (NCCN + Persistant Disease) | |
| no | 23 |
| yes | 17 |
| Pre-RP ADT | |
| no | 40 |
| yes | 0 |
| Metastasis (at time of RP) | |
| no | 38 |
| yes | 2 |

MBII-52 fwd: 5'-AATGATGACAACCCAATGTC (SEQ ID NO:7)
MBII-52 rev: 5'-GCCTCAGCGTAATCCTATT (SEQ ID NO:8)
MBII-52 probe: 5'-/56-FAM/AAGGTGATGACATAAAATTCATGCTC/36-TAMSp/
(SEQ ID NO:9)
MBII-52
Slope (m) = -3.57
Efficiency (E) = $(10^{-1/m} - 1) \times 100$ = 90.5%

SEQUENCE LISTING

```
<160> NUMBER OF SEQ ID NOS: 56

<210> SEQ ID NO 1
<211> LENGTH: 82
<212> TYPE: DNA
<213> ORGANISM: human
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 1
gggtcnatga tgagaacctt atattgtnct gaagagaggt gatgacttaa aaatcatgct      60 cataggatt angctgaggc cc                                                82

<210> SEQ ID NO 2
<211> LENGTH: 82
<212> TYPE: RNA
<213> ORGANISM: human
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (28)..(28)
<223> OTHER INFORMATION: n is a, c, g, or u
<220> FEATURE:
<221> NAME/KEY: misc_feature
<222> LOCATION: (72)..(72)
<223> OTHER INFORMATION: n is a, c, g, or u

<400> SEQUENCE: 2
gggucnauga ugagaaccuu auauuguncu gaagagaggu gaugacuuaa aaaucaugcu      60
caauaggauu angcugaggc cc                                               82

<210> SEQ ID NO 3
<211> LENGTH: 25
<212> TYPE: DNA
<213> ORGANISM: artificial sequence
<220> FEATURE:
<223> OTHER INFORMATION: PCR primer

<400> SEQUENCE: 3
atgagaacct tatattgtcc tgaag                                            25

<210> SEQ ID NO 4
<211> LENGTH: 18
<212> TYPE: DNA
<213> ORGANISM: artificial sequence
<220> FEATURE:
<223> OTHER INFORMATION: PCR primer

<400> SEQUENCE: 4
```

-continued

| | |
|---|---|
| ggcctcagcg taatccta | 18 |

<210> SEQ ID NO 5
<211> LENGTH: 26
<212> TYPE: DNA
<213> ORGANISM: artificial sequence
<220> FEATURE:
<223> OTHER INFORMATION: Human

<400> SEQUENCE: 5

| | |
|---|---|
| ggtgatgact taaaaatcat gctcaa | 26 |

<210> SEQ ID NO 6
<211> LENGTH: 73
<212> TYPE: DNA
<213> ORGANISM: human

<400> SEQUENCE: 6

| | |
|---|---|
| atgagaacct tatattgtcc tgaagagagg tgatgactta aaaatcatgc tcaataggat | 60 |
| tacgctgagg ccc | 73 |

<210> SEQ ID NO 7
<211> LENGTH: 20
<212> TYPE: DNA
<213> ORGANISM: artificial sequence
<220> FEATURE:
<223> OTHER INFORMATION: Mouse

<400> SEQUENCE: 7

| | |
|---|---|
| aatgatgaca acccaatgtc | 20 |

<210> SEQ ID NO 8
<211> LENGTH: 19
<212> TYPE: DNA
<213> ORGANISM: artificial sequence
<220> FEATURE:
<223> OTHER INFORMATION: Mouse PCR primer

<400> SEQUENCE: 8

| | |
|---|---|
| gcctcagcgt aatcctatt | 19 |

<210> SEQ ID NO 9
<211> LENGTH: 26
<212> TYPE: DNA
<213> ORGANISM: artificial sequence
<220> FEATURE:
<223> OTHER INFORMATION: Mouse primer

<400> SEQUENCE: 9

| | |
|---|---|
| aaggtgatga cataaaattc atgctc | 26 |

<210> SEQ ID NO 10
<211> LENGTH: 82
<212> TYPE: DNA
<213> ORGANISM: human

<400> SEQUENCE: 10

| | |
|---|---|
| gtgttgatga tgagaacctt atattatcct gaagagaggt gatgacttaa aaatcatgct | 60 |
| caataggatt acgctgaggc cc | 82 |

<210> SEQ ID NO 11
<211> LENGTH: 82
<212> TYPE: DNA

```
<213> ORGANISM: human

<400> SEQUENCE: 11
gggtcgatga tgagaagctt ctgttttctt gaagagaggt gatgacttaa aaatcatgct      60 cataggatt atgctgaggc cc                                                 82

<210> SEQ ID NO 12
<211> LENGTH: 82
<212> TYPE: DNA
<213> ORGANISM: human

<400> SEQUENCE: 12
gggtcaatga tgagaacctt atattgtcct gaagagaggt gatgacttaa aaatcatgct      60
tagtaggatt acgctgaggc ct                                                82

<210> SEQ ID NO 13
<211> LENGTH: 82
<212> TYPE: DNA
<213> ORGANISM: human

<400> SEQUENCE: 13
gggtcgatga tgagaacttt atattgttct gaagagaggt gatgacttaa aaatcatgct      60 cataggatt acgctgaggc cc                                                 82

<210> SEQ ID NO 14
<211> LENGTH: 82
<212> TYPE: DNA
<213> ORGANISM: human

<400> SEQUENCE: 14
ggatcgatga tgagaacctt atattgtcct gaagagaggt gatgacttaa aaatcatgct      60 cataggatt acgctgaggc cc                                                 82

<210> SEQ ID NO 15
<211> LENGTH: 82
<212> TYPE: DNA
<213> ORGANISM: human

<400> SEQUENCE: 15
gggtcaatga tgagaacctt atattgttct gaagagaggt gatgacttaa aaatcatgct      60 cataggatt acgctgaggc cc                                                 82

<210> SEQ ID NO 16
<211> LENGTH: 82
<212> TYPE: DNA
<213> ORGANISM: human

<400> SEQUENCE: 16
gggtcaatga gaaccttata ttgtcctgaa gagaggtgat aacttaaaaa tcatgctcaa      60
taataggatt acgctgaggc cc                                                82

<210> SEQ ID NO 17
<211> LENGTH: 85
<212> TYPE: DNA
<213> ORGANISM: human

<400> SEQUENCE: 17
gggtcaatga tgagaacctt acattgttct gaagagagat gatgacttaa aaatcatgct      60 cataatagg attacgctga ggccc                                              85
```

<210> SEQ ID NO 18
<211> LENGTH: 82
<212> TYPE: DNA
<213> ORGANISM: human

<400> SEQUENCE: 18
gggtcgatga tgagaaacctt atattgtcct gaagagaggt gatgacttaa aaatcatgct    60
caataggatt acgctgaggc cc                                              82

<210> SEQ ID NO 19
<211> LENGTH: 81
<212> TYPE: DNA
<213> ORGANISM: human

<400> SEQUENCE: 19
gggtcgatga tgagaacctt atattgtctg aagagaggtg atgacttaaa aatcatgctc    60
aataggatta cgctgaggcc c                                              81

<210> SEQ ID NO 20
<211> LENGTH: 82
<212> TYPE: DNA
<213> ORGANISM: human

<400> SEQUENCE: 20
gggtcaatga tgagaacctt atattgtcct gaagagaggt gatgacttaa aaatcatgct    60
caataggatt acgctgaggc cc                                              82

<210> SEQ ID NO 21
<211> LENGTH: 82
<212> TYPE: DNA
<213> ORGANISM: human

<400> SEQUENCE: 21
gggtcgatga tgagaacctt atattgtcct gaagagaggt gatgacttaa aaatcatgct    60
caataggatt acgctgaggc cc                                              82

<210> SEQ ID NO 22
<211> LENGTH: 82
<212> TYPE: DNA
<213> ORGANISM: human

<400> SEQUENCE: 22
gggtcgatga tgagaacctt atattatcct gaagagaggt gatgacttaa aaatcatgct    60
caataggatt acgctgaggc cc                                              82

<210> SEQ ID NO 23
<211> LENGTH: 81
<212> TYPE: DNA
<213> ORGANISM: human

<400> SEQUENCE: 23
gggtcgatga tgagaaactt atattgtctg aagagaggtg atgacttaaa aatcatgctc    60
aataggatta cgctgaggcc c                                              81

<210> SEQ ID NO 24
<211> LENGTH: 81
<212> TYPE: DNA
<213> ORGANISM: human

```
<400> SEQUENCE: 24
gggtcgatga tgagaacctt atatgttctg aagagaggtg atgacttaaa aatcatgctc      60
aataggatta cgctgaggcc c                                                81

<210> SEQ ID NO 25
<211> LENGTH: 82
<212> TYPE: DNA
<213> ORGANISM: human

<400> SEQUENCE: 25
gggtcaatga tgagaacctt atattatcct gaagagaggt gatgacttaa aaatcatgct      60
caataggatt acgctgaggc cc                                               82

<210> SEQ ID NO 26
<211> LENGTH: 82
<212> TYPE: DNA
<213> ORGANISM: human

<400> SEQUENCE: 26
gggtcgatga tgagaacctt atattgtcct gaagagaggt gatgacttaa aaatcattct      60
caaaaggatt atgctgaggc cc                                               82

<210> SEQ ID NO 27
<211> LENGTH: 82
<212> TYPE: DNA
<213> ORGANISM: human

<400> SEQUENCE: 27
gggtcgatga tgagaacctt atattgtcct gaagagaggt gatgacttaa aaatcattct      60
caaaaggatt atgctgaggc cc                                               82

<210> SEQ ID NO 28
<211> LENGTH: 82
<212> TYPE: DNA
<213> ORGANISM: human

<400> SEQUENCE: 28
gggtcgatga tgagaacctt atattgtcct gaagagaggt gatgacttaa aaatcattct      60
caaaaggatt atgctgaggc cc                                               82

<210> SEQ ID NO 29
<211> LENGTH: 82
<212> TYPE: DNA
<213> ORGANISM: human

<400> SEQUENCE: 29
gggtcgatga tgagaacctt atattgtcct gaagagaggt gatgacttaa aaatcatgct      60
caataggatt atgctgaggc cc                                               82

<210> SEQ ID NO 30
<211> LENGTH: 81
<212> TYPE: DNA
<213> ORGANISM: human

<400> SEQUENCE: 30
gggtcgatga tgagaacctt atattttctg aagagaggtg atgacttaaa aatcatgctc      60
aataggatta cgctgaggcc c                                                81
```

```
<210> SEQ ID NO 31
<211> LENGTH: 82
<212> TYPE: DNA
<213> ORGANISM: human

<400> SEQUENCE: 31
gggtcaatga tgagaacctt atattgtcct gaagagaggt gatgacttaa aaatcatgct      60
caataggatt acgctgagtc cc                                               82

<210> SEQ ID NO 32
<211> LENGTH: 82
<212> TYPE: DNA
<213> ORGANISM: human

<400> SEQUENCE: 32
gggtcaatga tgagaaccct atattgtgtt gaagagaggt gatgacttaa aattaccatg      60
ctcaatgatt acgctgaggc cc                                               82

<210> SEQ ID NO 33
<211> LENGTH: 71
<212> TYPE: DNA
<213> ORGANISM: human

<400> SEQUENCE: 33
gagaacctta tattgttctg aagagaggtg gtgacttaaa atcatgctc aataggatta      60 cgctgaggcc c                                                           71

<210> SEQ ID NO 34
<211> LENGTH: 82
<212> TYPE: DNA
<213> ORGANISM: human

<400> SEQUENCE: 34
aggtcgatta tgagaacctt atattgtcct gaagagaggt gatgacttaa aaatcatgcc      60
caataggatt acgctgaggc cc                                               82

<210> SEQ ID NO 35
<211> LENGTH: 82
<212> TYPE: DNA
<213> ORGANISM: human

<400> SEQUENCE: 35
gggtcagtga tgagaacctt atattgtcct gaagagaggt gatgacttaa aaatcatgct      60
caataggatt acgctgaggc cc                                               82

<210> SEQ ID NO 36
<211> LENGTH: 76
<212> TYPE: DNA
<213> ORGANISM: human

<400> SEQUENCE: 36
atgatgagaa ccttatattg tcctgaaaag aggtgatgac ttaacaatca tgctcaatag      60
gattacattg aagccc                                                      76

<210> SEQ ID NO 37
<211> LENGTH: 75
<212> TYPE: DNA
<213> ORGANISM: human

<400> SEQUENCE: 37
```

```
tgatgagaac cttgtattct tctgaagaga ggtgatgact taaaaaccat gctcaatagg      60
attacactta ggccg                                                      75

<210> SEQ ID NO 38
<211> LENGTH: 82
<212> TYPE: DNA
<213> ORGANISM: human

<400> SEQUENCE: 38
gggtcaatga tgagaacctt atattgtcct gaagagaggt gatgacttaa aaatcatgct      60
caataggatt acgctgaggc cc                                              82

<210> SEQ ID NO 39
<211> LENGTH: 82
<212> TYPE: DNA
<213> ORGANISM: human

<400> SEQUENCE: 39
gggtcaatga tgagaacctt atattgttct gaagagaggt gattatttaa aaatcatgct      60
caataggatt acgctgaggc cc                                              82

<210> SEQ ID NO 40
<211> LENGTH: 82
<212> TYPE: DNA
<213> ORGANISM: human

<400> SEQUENCE: 40
gggtcagtga tgagaacctt atattgtcct gaagaaaggt gatgacttaa aaatcatgct      60
caataggatt acactgaggc cc                                              82

<210> SEQ ID NO 41
<211> LENGTH: 82
<212> TYPE: DNA
<213> ORGANISM: human

<400> SEQUENCE: 41
gggtcaatga tgagaacctg atattgccct gaagagagat gatgacttaa aaatcatgtt      60
caataggatt acgctgaggc ct                                              82

<210> SEQ ID NO 42
<211> LENGTH: 82
<212> TYPE: DNA
<213> ORGANISM: human

<400> SEQUENCE: 42
gggtcaatga tgagaaccgt atattgtcct gaagagcggt gatgacttaa aaataatgct      60
caataggatt acgctgaggc cc                                              82

<210> SEQ ID NO 43
<211> LENGTH: 82
<212> TYPE: DNA
<213> ORGANISM: human

<400> SEQUENCE: 43
gggtcaatga tgagaacctt ataatgttct gaagagaggt gatgacttaa aaatcatgct      60
caataggatt acgctgaggc cc                                              82

<210> SEQ ID NO 44
<211> LENGTH: 82
```

```
<212> TYPE: DNA
<213> ORGANISM: human

<400> SEQUENCE: 44
gggtcaatga tgagaacctt gtattatctt gaagagaggt gatgacttaa aaatcatgct    60 cataggatt  acactgaggc cc                                            82

<210> SEQ ID NO 45
<211> LENGTH: 82
<212> TYPE: DNA
<213> ORGANISM: human

<400> SEQUENCE: 45
gggtcaatga tgagaacctt atattgtcct gaagagaggt gatgacttaa aaatcatgct    60 cataggatt  acgctgaggc cc                                            82

<210> SEQ ID NO 46
<211> LENGTH: 82
<212> TYPE: DNA
<213> ORGANISM: human

<400> SEQUENCE: 46
gggctgatga tgagaacctt atattgtcct gaaaaaaggt gatgacttaa acatcatgct    60
taatagtatt atgctgaagc cc                                            82

<210> SEQ ID NO 47
<211> LENGTH: 82
<212> TYPE: DNA
<213> ORGANISM: human

<400> SEQUENCE: 47
gggtcaatga tgagaacctt acattgtcct gaagagagat gatgacttaa aaatcatgct    60 cataggatt  acgctgaggc cc                                            82

<210> SEQ ID NO 48
<211> LENGTH: 82
<212> TYPE: DNA
<213> ORGANISM: human

<400> SEQUENCE: 48
gggtcaatga tgagaatctt atattgtcct gaagagaggt gatgacttaa aaatcatgct    60 cataggatt  acgctgaggc cc                                            82

<210> SEQ ID NO 49
<211> LENGTH: 82
<212> TYPE: DNA
<213> ORGANISM: human

<400> SEQUENCE: 49
gggtcgatga tgagaacctt atattttcct gaagagaggt gatgacttaa aaatcatgct    60 cataggatt  acgctgaggc cc                                            82

<210> SEQ ID NO 50
<211> LENGTH: 82
<212> TYPE: DNA
<213> ORGANISM: human

<400> SEQUENCE: 50
gggtcagtga tgagaacctt ctattgtcct gaagagaggt gatgacttaa aaatcatgct    60
```

```
caataggatt acgctgaggc cc                                              82

<210> SEQ ID NO 51
<211> LENGTH: 82
<212> TYPE: DNA
<213> ORGANISM: human

<400> SEQUENCE: 51
gggtcgatga tgagaacctt atattgttct gaagagaggt gatgacttaa aaatcatgct    60
caataggatt acgctgaggc cc                                              82

<210> SEQ ID NO 52
<211> LENGTH: 82
<212> TYPE: DNA
<213> ORGANISM: human

<400> SEQUENCE: 52
gggtcaatga tgagaacctt atattgtcct gaagagaggt gatgacttaa aaatcatgct    60
caataggatt acgctgaggc cc                                              82

<210> SEQ ID NO 53
<211> LENGTH: 82
<212> TYPE: DNA
<213> ORGANISM: human

<400> SEQUENCE: 53
gggtcaatga tgagaacctt atattgtcct gaagagcggt gatgacttaa aaatcatgct    60
caataggatt acgctgaggc cc                                              82

<210> SEQ ID NO 54
<211> LENGTH: 53
<212> TYPE: DNA
<213> ORGANISM: human

<400> SEQUENCE: 54
ttatattgtc ttcgacaggg aagatgacat aaaaattatg ttcaatagga tta           53

<210> SEQ ID NO 55
<211> LENGTH: 35
<212> TYPE: DNA
<213> ORGANISM: human

<400> SEQUENCE: 55
gtaaaaatca tgctcaatag aattaagctg aggct                               35

<210> SEQ ID NO 56
<211> LENGTH: 75
<212> TYPE: DNA
<213> ORGANISM: human

<400> SEQUENCE: 56
gggtcaatga tgagatgtta cttgaagaga aatgatgacg taaaaattaa gttcagttgg    60
attacgctga ggccc                                                      75
```

METHODS FOR DIAGNOSING CANCER BASED ON SMALL NUCLEOLAR RNA HBII-52

CROSS REFERENCE TO RELATED APPLICATIONS

This application claims priority to U.S. provisional patent application No. 61/750,554, filed Jan. 9, 2013.

STATEMENT REGARDING FEDERAL FUNDING

This invention was made with government support under CA095367 awarded by the National Institutes of Health. The government has certain rights in the invention.

FIELD

This disclosure relates generally to cancer diagnostics and more particularly to use of snoRNA HBII-52 for diagnosis or aiding in the diagnosis of certain cancers.

BACKGROUND

Small Nucleolar RNAs (snoRNAs) are non-coding RNAs involved in RNA processing (1). There are two major subclasses of snoRNAs, termed box C/D and box H/ACA snoRNAs. These two classes contain guide sequences that are known to canonically pair with complementary regions on a target pre-rRNA, forming a RNA duplex and facilitating the enzymatic activity of methylases and uridylases that site specifically modify pre-rRNA bases by either 2'-O-methylation or pseudouridylation respectively. These modifications of the rRNA are critical to ribosome assembly and viability. In the last decade, various orphan snoRNAs have been identified that structurally resemble C/D box snoRNAs but do not contain sequence complementarity to rRNA. While some snoRNAs and other non-coding RNAs have been implicated in diseases or other disorders, there remains an ongoing need to identify, characterize and develop compositions and methods which harness the involvement of snoRNAs for diagnosis and therapy of such diseases and disorders.

SUMMARY OF THE DISCLOSURE

In various embodiments, the present disclosure relates to compositions and methods for detecting in a sample the presence or absence, and/or the amount, of a small nucleolar RNA (snoRNA) HBII-52 (also known as SNORD115). The compositions and methods are useful in diagnosis, prognosis, therapy recommendations, therapy, and monitoring of therapy for individuals who have a disorder that is positively correlated with elevated HBII-52. In embodiments, the disorder is a cancer. In certain embodiments, the cancer is prostate cancer.

FIG. 13 provides 47 polynucleotide sequences that are known HBII-52 variants. This disclosure includes detection of a polynucleotide(s) which comprises or consist of any of the sequences presented in FIG. 13 and their RNA equivalents, and any combination(s) thereof, using any suitable technique. FIG. 13 also presents HBII-52 consensus sequences as SEQ ID NO:1 (DNA) and SEQ ID NO:2 (RNA). In embodiments, this disclosure includes detecting and/or quantitating HBII-52 by measuring a polynucleotide having SEQ ID NO:1 or SEQ ID NO:2 as further described herein. In embodiments, kits comprising primers for detecting and/or amplifying HBII-52 from a biological sample are provided. The 47 sequences in FIG. 13 represent SEQ ID NOs: 10-SEQ ID NO:56, respectively.

In one embodiment the disclosure includes a method for diagnosing an individual as having cancer comprising testing in vitro a biological sample obtained from the individual for the presence of HBII-52, comparing the amount of HBII-52 to the amount of HBII-52 in a non-cancer control, and determining an amount of HBII-52 in the sample that is greater than the amount of HBII-52 in the non-cancer control, thereby diagnosing the individual as having the cancer. In embodiments, the sample is a sample of prostate tissue obtained from the individual. In an embodiment, the individual is diagnosed as having an aggressive form of prostate cancer and/or castration recurrent prostate cancer. In embodiments, the method comprises amplification of an HBII-52 sequence using a polymerase chain reaction (PCR), where the PCR comprises amplifying the HBII-52 using a first primer which comprises or consists of SEQ ID NO:3 and a second primer which comprises or consists of SEQ ID NO:4.

In another aspect the disclosure includes a method for monitoring an individual undergoing therapy for a disorder associated with HBII-52 expression. The method comprises obtaining a first sample from the individual and testing it to determine a first amount of HBII-52, treating the individual with a therapeutic agent intended to treat the disorder, obtaining a second biological sample from the individual and testing it determine a second amount of HBII-52. A reduction in the amount of HBII-52 in the second biological sample relative to the amount of HBII-52 in the first biological sample indicates the therapy is effective. Conversely, a lack of reduction of the HBII-52 in the second biological sample relative to the amount of the HBII-52 in the first biological sample indicates the therapy is not effective. In embodiments, the individual is undergoing therapy for prostate cancer.

In another aspect the disclosure includes a method comprising testing a biological sample from an individual for HBII-52, determining elevated HBII-52 in the biological sample relative to a control, and administering to the individual at least one therapeutic agent effective for treating at least one disorder associated with the presence of the HBII-52 in the sample. In an embodiment the disorder is prostate cancer. In an embodiment, the therapeutic agent is an antagonist of $5\text{-HT}_{2c}R$, such as but not limited to SB 242,084.

In another aspect a method for therapy of a subject diagnosed with prostate cancer is provided. The method comprises administering to the subject a composition comprising a therapeutically effective amount of an antagonist of $5\text{-HT}_{2c}R$.

BRIEF DESCRIPTION OF THE DRAWINGS

FIG. 13. Consensus sequence and alignment of representative sequences.

FIG. 19 Summary of clinical samples and associated data utilized for evaluation of HBII-52 expression from clinical specimens. Normal control tissues were prostate tissue samples obtained during cystoprostatectomies in bladder cancer patients.

DESCRIPTION

Figure 1:
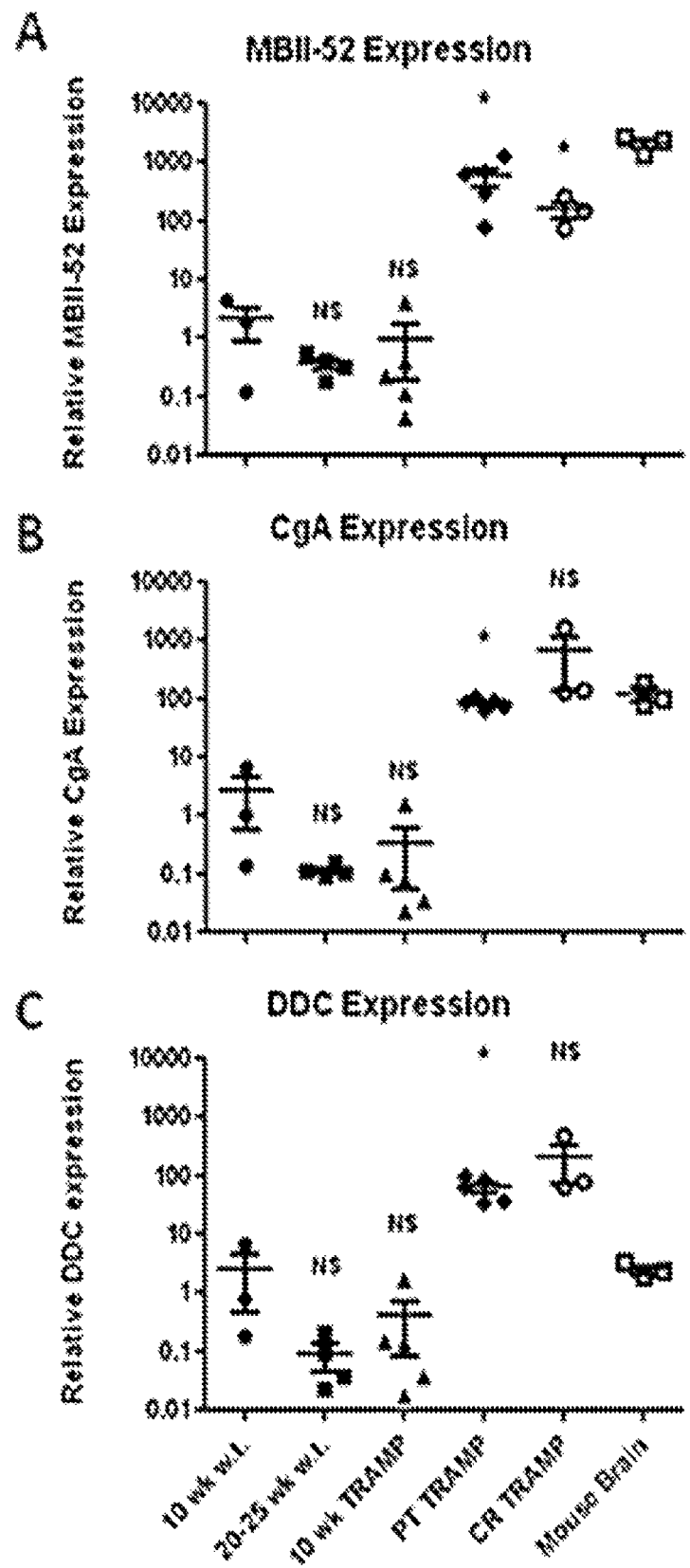
FIG. 1 Expression of A) MBII-52, B) chromogranin A (CgA), and C) dopa decarboxylase (DDC). All are normalized to endogenous control BGus, and displayed relative to 10 week wildtype (w.t.). MBII-52 is expressed at low levels in the prostate of young and old wild type mice. Expression of snoRNA MBII-52 increases by several orders of magnitude in TRAMP mice with palpable tumors. Also, castration recurrent TRAMP tumors that recurred after castration at 12 weeks display markedly high levels of MBII-52. Putative NE markers CgA and DDC also correlate with progression and MBII-52 expression. Two-tailed unpaired t-tests were conducted comparing all sample sets (except brain, positive control) with 10 week w.t. NS: p>0.05 and *: p<0.05

In this disclosure we use mouse and human samples to demonstrate that HBII-52 is correlated with malignant phenotypes. In particular we show, among other data, that HBII-52 expression is elevated in human clinical PCa samples, HBII-52 expression is increased with increasing pathological tumor stage, HBII-52 expression is increased with increasing PCa aggression, HBII-52 expression is increased with increasing pathological Gleason score; and HBII-52 expression is increased in patients that had biochemical failure.

In one aspect the present disclosure provides compositions and methods that relate to analysis of a snoRNA. In particular embodiments, the method comprises detecting in a sample in vitro the presence or absence, and/or the amount, of a small nucleolar RNA (snoRNA) HBII-52 (also known as SNORD115), or a precursor thereof, or a fragment thereof. In certain embodiments, the sample is a biological sample obtained or derived from a human subject.

In another aspect, the method comprises determining the presence or absence, and/or the amount of HBII-52 in a sample to develop a treatment recommendation for an individual, and/or to determine the severity of a particular disease or disorder that is positively correlated with the presence of HBII-52, and/or to monitor the efficacy of a treatment for such a disease or disorder. The methods generally comprise testing a sample obtained or derived from an individual for the presence or absence, and/or the amount of HBII-52, and determining from the presence or absence, and/or the amount of HBII-52 whether or not an individual has a particular disease or disorder associated with HBII-52 expression, or the severity of such disease or disorder, or whether the individual is a candidate for treatment of a disease or disorder associated with HBII-52 expression, or whether a therapy for the disease or disorder for which the individual is undergoing is effective. The amount of HBII-52 in a sample can be measured and/or compared against any suitable reference, such as an established normal range, a standardized curve, and/or experimentally designed controls such as known input RNA or used to normalize experimental data for qualitative or quantitative determination of the HBII-52 in the sample for mass, molarity, concentration and the like. The reference level may also be depicted graphically as an area on a graph In embodiments, an amount of HBII-52 in a test sample that is higher than the amount of HBII-52 in a non-cancer control sample is a diagnosis or aids in a diagnosis of a cancer described herein. In embodiments, an amount of HBII-52 in a test sample that is greater than the highest amount of HBII-52 in a sample that is part of a group of non-cancer control cells is a diagnosis or aids in a diagnosis of a cancer described herein. In embodiments, an amount of HBII-52 that is greater than the highest amount of HBII-52 in a range of HBII-52 amounts established from normal control samples is a diagnosis or aids in a diagnosis of cancer. In certain embodiments, determining the amount of HBII-52 is performed prior to and/or after administering to the individual an agent intended to treat a disease or disorder associated with HBII-52 expression.

The invention can be used to determine HBII-52 in any sample. In certain embodiments, the presence or absence or amount of HBII-52 can be detected in a biological sample or in a preparation derived from a biological sample. The biological sample can be tested directly, or it can be subjected to a processing step to isolate, amplify or purify components of the sample. In non-limiting embodiments, HBII-52 could be detected from saliva, blood, urine, hair, skin, buccal swab, or any other sample that contains or would be suspected to contain snoRNA, or a precursor thereof, or a polynucleotide product made by cleavage of a snoRNA. The sample can be taken from the individual using any of various methods which are known in the art for obtaining biological samples from a patient. In certain embodiments, the sample comprises a sample which contains or is suspected of containing cancer cells. In certain embodiments, the sample can be a tumor sample. Specific examples of cancers and tumor types which can be assessed using the invention include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell cancers of any kind, including but not limited to lung carcinoma, pancrease, prostate, and kidney, bladder carcinoma, epithelial carcinoma, astrocytoma, medulloblastoma, glioblastoma, primitive neuroectodermal tumor, choroid plexus carcinoma, choroid plexus papilloma, craniopharyngioma, ependymoma, pinealoma, hemangioblastoma, acoustic neuroma, oliodendroglioma, meningioma, melanoma, neuroblastoma, retinoblastoma, thymoma, Waldenstrom's macroglobulinemia, and heavy chain disease. In one embodiment, the sample is a sample of prostate tissue or prostate cancer. In certain embodiments, the sample is not obtained or derived from an individual who has a blood cancer, such as multiple myeloma (MM) or leukemia, such as chronic lymphocytic leukemia (CLL). In certain embodiments, the sample is free of MM or CLL cells, and/or combinations thereof. In certain embodiments, the sample is a sample of brain tissue or prostate tissue and is obtained from an individual who has a brain cancer or a prostate cancer, respectively. In a particular embodiment, the sample is obtained from a human subject who has or is at risk for developing prostate cancer. In embodiments, the sample comprises prostate cancer (PCa). In an embodiment, the prostate cancer is castration-resistant prostate cancer (CR-PCa).

In one embodiment, the disclosure includes a method of diagnosing or aiding in the diagnosis of prostate cancer, comprising: obtaining a nucleic acid-containing test sample from a subject suspected of having or diagnosed with prostate cancer, wherein the sample comprises prostate cells; measuring the level of HBII-52 in the test sample; comparing the level of HBII-52 in the test sample from the subject to a control level of HBII-52 in a sample from non-cancerous prostate; and diagnosing the subject as having an aggressive form of prostate cancer, and/or a worse prognosis relative to a prostate cancer patient who does not have elevated HBII-52, if the level of the HBII-52 in the test sample from the subject is greater than the control level for the HBII-52.

HBII-52 is known in the art. As will be apparent from FIG. 13 and the existing art, HBII-52 has multiple genomic copies arranged in tandem which vary from one another by way of single nucleotide variants, insertions, deletions, and combinations thereof. In particular embodiments, the invention is suited to detect any of the 47 polynucleotide sequences presented in FIG. 13 in the enumerated list individually, or any combination of those 47 sequences. In certain aspects, the invention encompasses detection of a polynucleotide comprises or consists of the RNA equivalent of any of the polynucleotide sequences presented in FIG. 13. Any suitable technique can be used to detect the presence or absence of HBII-52. In non-limiting examples, suitable techniques include the use of polymerase-chain based reactions, such as PCR or quantitative (real-time) PCR (qPCR), or reverse-transcriptase based PCR (RT-PCR), or quantitative Reverse Transcription Polymerase Chain Reaction (qRT-PCR). These processes involve well known techniques and generally include providing a composition comprising isolated nucleic acids for testing and mixing with non-naturally occurring reagents, such as recombinant or isolated bacterial, viral or bacteriophage polymerases, buffers comprising pre-fixed concentrations of free deoxyribonucleotides, including those that are unlabeled and/or those that are detectably labeled, and/or recombinant bacterial restriction endonucleases, and combinations of the foregoing. These compositions can comprise one or more synthetic oligonucleotides that have complete or partial complementarity to HBII-52 sequences so that they can function as probes, such as for hybridization used in detection of the HBII-52 sequences, and/or for amplification techniques. In another embodiment, isolated polynucleotides which have complete or partial complementarity to HBII-52 can be annealed to a synthetic oligonucleotide that is fixed to a substrate, such as glass, or resin, or any other substrate. For example, isolated polynucleotides which have complete or partial complementarity to HBII-52 can be present on an array which comprises a plurality of distinct oligonucleotides. Such arrays can be used in commercially available methods and devices to determine the presence or absence of HBII-52, as well to determine relative amounts of it. As such, the invention includes array and chip-based assays to determine HBII-52. In various embodiments, PCR-based amplification techniques are utilized with primers that can amplify all, or any combination or subcombination of the RNA equivalents of the polynucleotide sequences depicted in FIG. 13.

As discussed above, the invention includes detecting any version of HBII-52, examples of which are shown in FIG. 13 (with the understanding that FIG. 13 presents genomic sequences; thus, each polynucleotide sequence presented in FIG. 13 encompasses its RNA equivalent; i.e., the invention includes detecting each polynucleotide sequence, and any combination of them in FIG. 13, wherein each T is replaced by U). In FIG. 13, in the sequences numbered 1-47, single nucleotide differences or insertion/deletion sites are shaded to shown differences between the tandem copies. In the consensus sequence shown in FIG. 13, conserved positions are shown in bold and enlarged font and locations of low variability (mostly conserved positions) are shown by italicized R and Y. The enumerated as 6, 9, 10, 11, 12, 42 and 43 in FIG. 13 represent fully conserved sequences. In more detail, the consensus sequence shown in FIG. 13 is: GGGT-CRATGATGAGAACCTTATATTGTYCTGAAGAGAG-GTGATGACTTAAAAATCA TGCTCAATAGGAT-TAYGCTGAGGCCC (SEQ ID NO:1) and its RNA equivalent is: GGGUCRAUGAUGAGAACCUUAUAUU-GUYCUGAAGAGAGGUGAUGACUUAAAAAU CAUGCUCAAUAGGAUUAYGCUGAGGCCC (SEQ ID NO:2). In SEQ ID NO:1 and SEQ ID NO:2, "R" and "Y" indicate positions of frequently conserved nucleotides, but in certain embodiments either or both R and Y can be any of C, A, G or T (wherein the T is U in the RNA sequence of SEQ ID NO:2). In certain embodiments, the R is G or A. In certain embodiments, the first Y (at nucleotide position 28) is T and the second Y (at nucleotide position 72) is C or T (U in the RNA sequence). Thus, in embodiments, in SEQ ID NO:1 and SEQ ID NO:2, the nucleotide at position 7 is G or A, and/or the nucleotide at position 28 is T, and/or the nucleotide at position 72 is C or U (where the U is T in the DNA sequence of SEQ ID NO:1), or any combination of such substitutions. In the sequence listing accompanying this disclosure, the R and Y in SEQ ID NO:1 and SEQ ID NO:2 are designated as "n" meaning they can be any nucleotide according to conventional sequence listing nomenclature.

Figure 14:
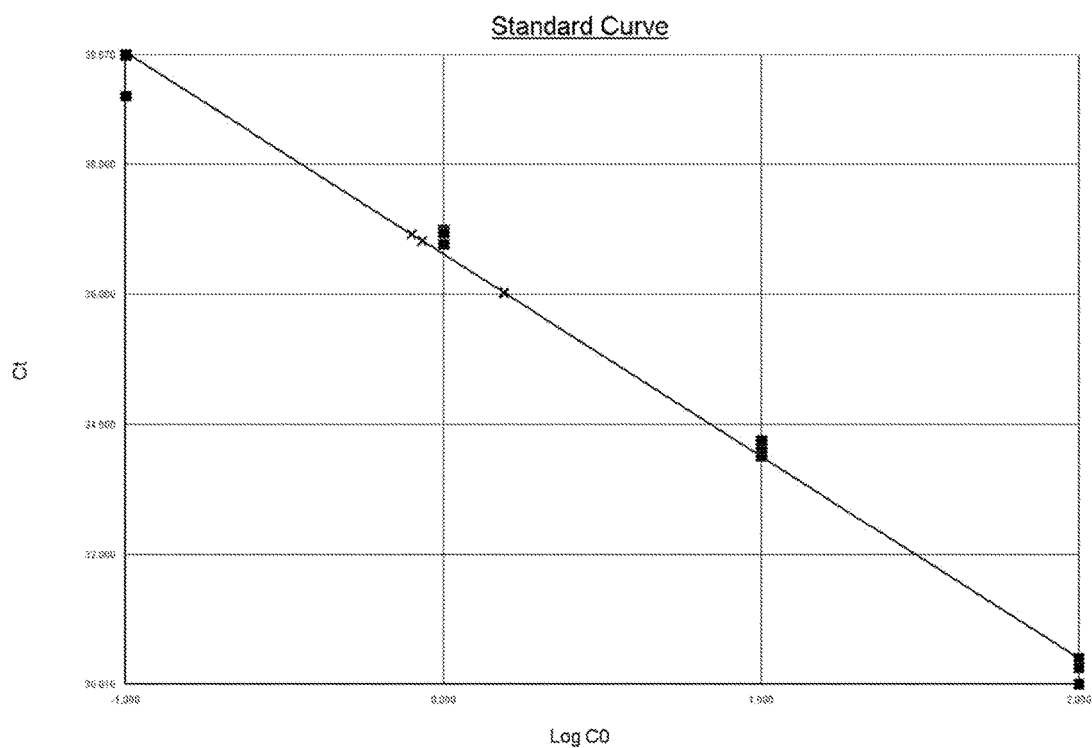
FIG. 14. Design and validation of human HBII-52 primers. Standard curves were generated from qPCR reactions from 1/10 serial dilutions of cDNA libraries generated from RNA isolated from mouse brain tissue. All qPCR experiments from cell lines and mouse tissue were conducted in 20 μL reaction volumes in 96-well format on an ABI 7300 real time PCR system (ABI, location). Each sample was aliquoted in triplicate into half skirt 96-well PCR plates (VWR, location), followed by primer/probe mixes and Taqman universal PCR mastermix, no AMPerase UNG (maker, location), and then sealed with clear adhesive film. 40 cycles of standard protocol qPCR were run with annealing temperatures of 55° C. for HBII-52 and MBII-52, and 60° C. for all other primers. Gene expression was normalized using ΔΔCT method to an appropriate endogenous control as indicated.
Figure 15:
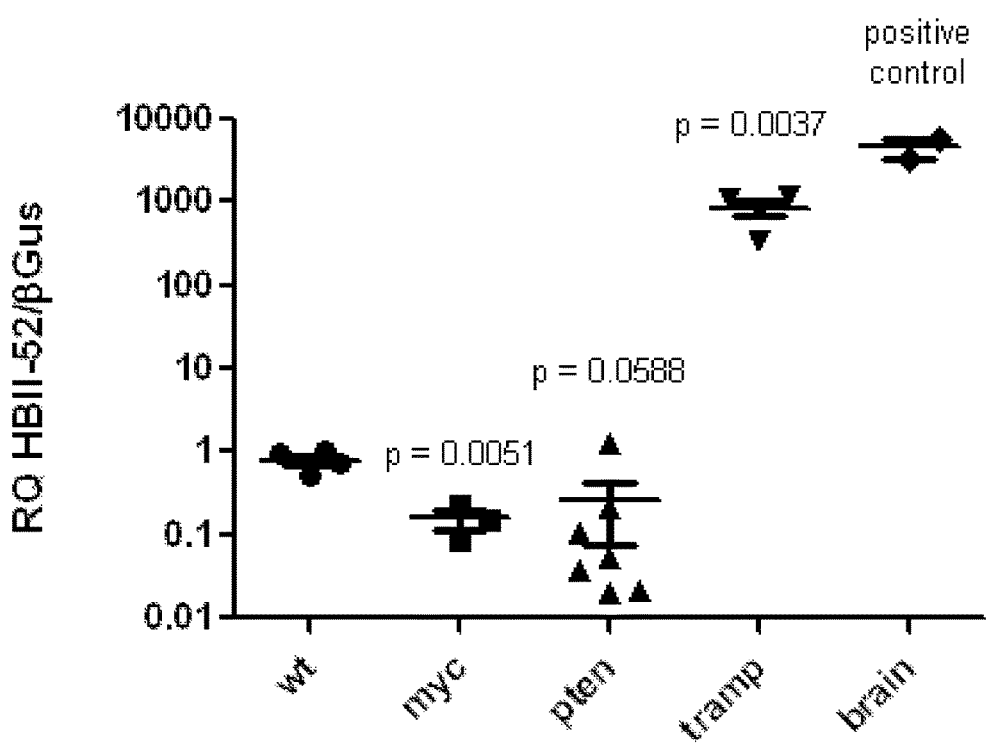
FIG. 15. Expression of MBII-52 in various PCa transgenic mouse models. TRAMP tumors express distinctly high levels of MBII-52 relative to other popular transgenic prostate cancer models such as prostate specific PTEN$^{-/-}$ (pten) and Hi-myc (myc) models. The expression of MBII-52 in PTEN$^{-/-}$ is highly variable and appears to correlate with tumor stage (see FIG. 3), whereas Hi-myc tumors have consistently lower HBII-52 then wildtype (FVB:C57Bl/6) prostates.
Figure 16:
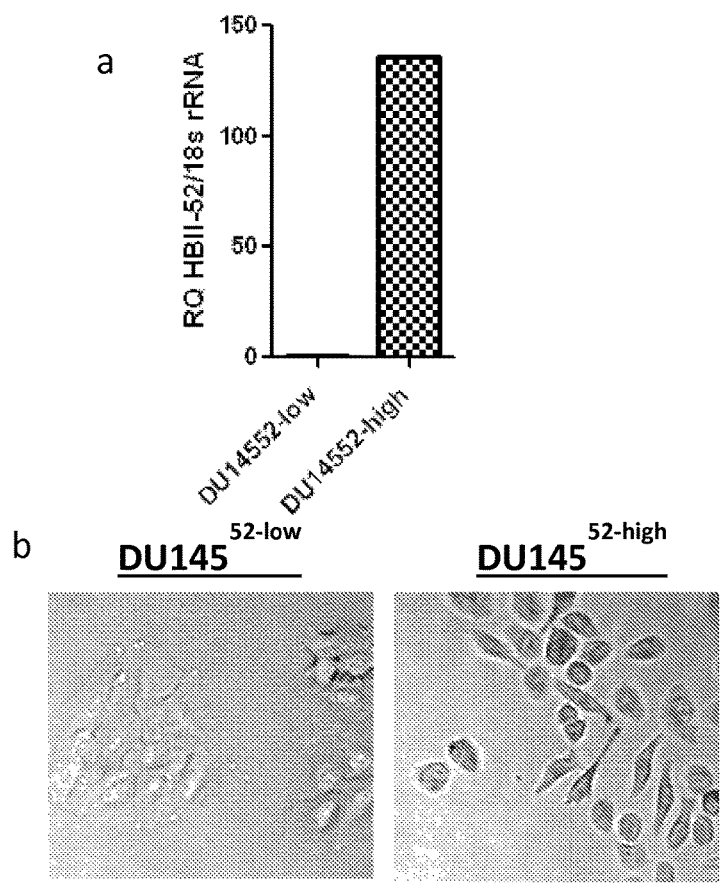
FIG. 16. HBII-52 overexpression in human PCa cell line DU145. A) Stable, clonal cell lines were generated. DU145$^{52\text{-}high}$ cells had >130-fold higher HBII-52 expression then DU145$^{52\text{-}high}$ control clonal cells. B) Phase-contrast microscopic images of DU145$^{52\text{-}high}$ and DU145$^{52\text{-}low}$ cells showing distinct morphologies. DU145$^{52\text{-}low}$ cells were more epithelial as evidenced by more obvious cell-to-cell adhesion and formation of monolayer, flattened clusters, in contrast with DU145$^{52\text{-}low}$ cells that appeared more rounded and aggressive.
Figure 17:
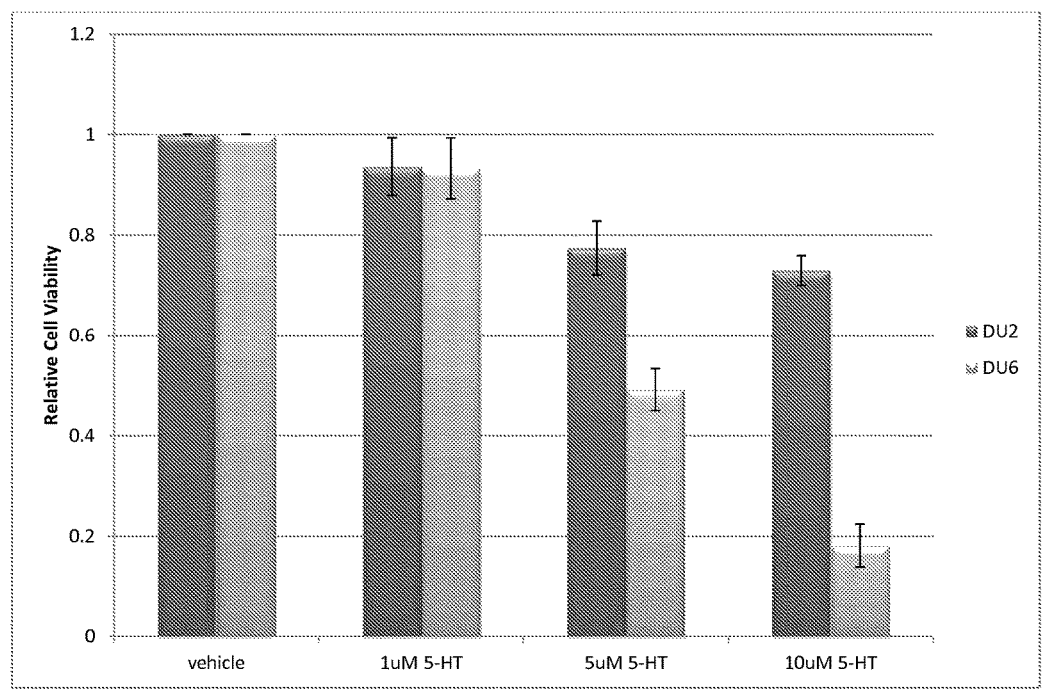
FIG. 17. Overexpression of HBII-52 affects cell viability in response to 5-HT treatment. The HBII-52 overexpressing cell line, DU6, has increased cytotoxic response to high concentrations of serotonin (5-HT) compared to the low expressing isogenic clone, DU2. Data are represented as the average+/−SEM of 3 independent experiments FIG. 18. Induction of HBII-52 expression in a medulloblastoma cell line, Daoy, results in Erk Activation. A stable cell line was generated from the parental medulloblastoma cell line, Daoy, using the T-REx™ System for inducible gene expression in order to evaluate the time-dependant consequences of elevated HBII-52 expression. A) A stable isolated clone, DAOY6, exhibited time-dependant inducibility of greater than 4-fold within 24 h. B) Western blot for phospho-Erk and total Erk indicated an increased activation of Erk as HBII-52 expression increased. The bands on the western blot were quantified using densitometry and p-Erk was normalized to t-Erk.
Figure 18:
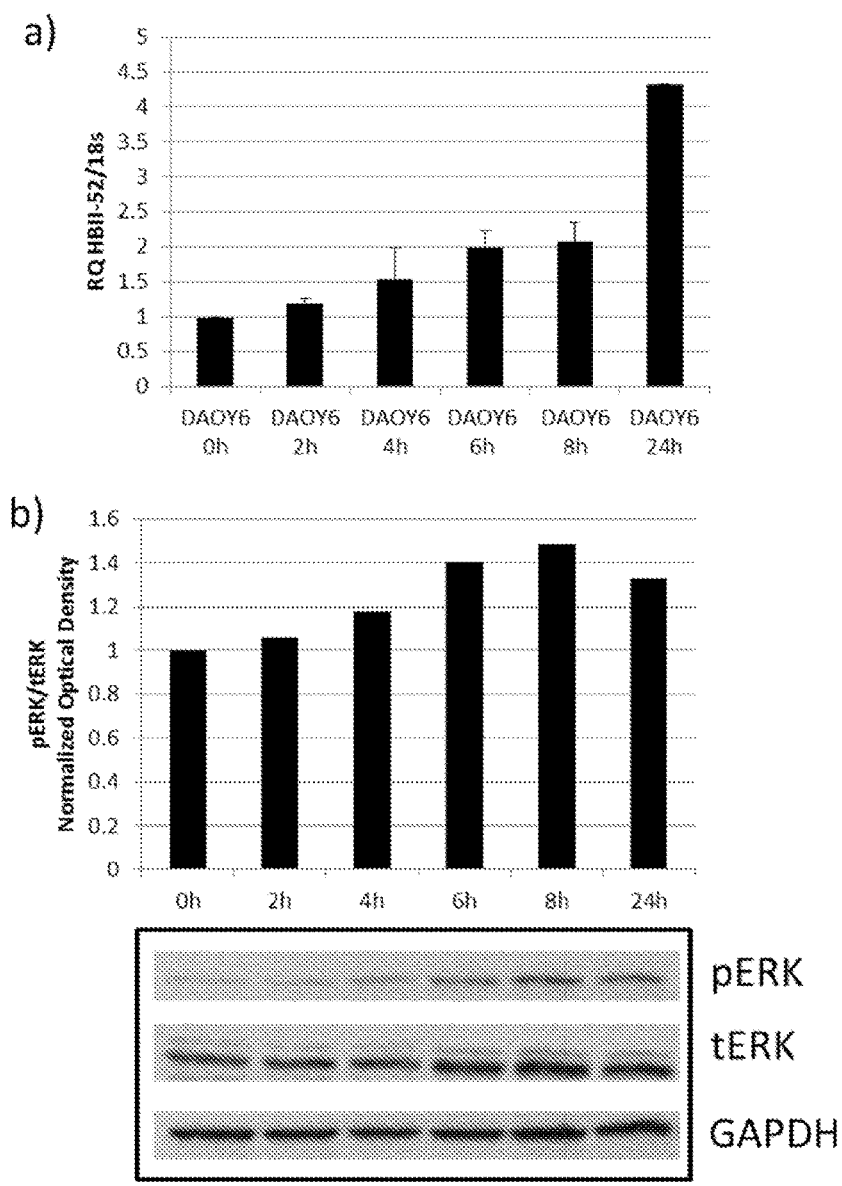
Figure 20:
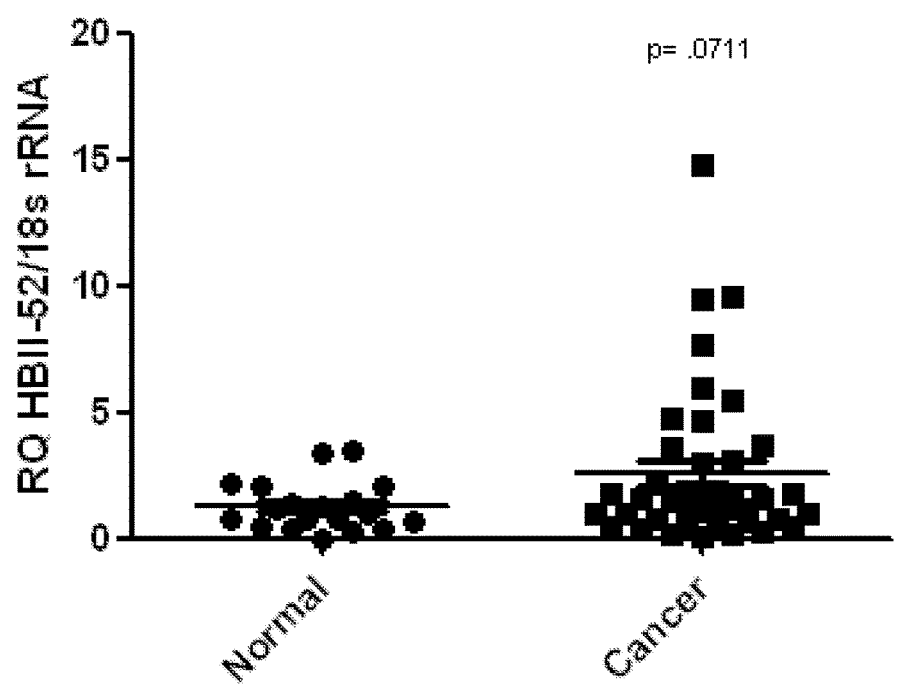
FIG. 20. HBII-52 expression is elevated in human clinical PCa samples. qRT-PCR for HBII-52 and 18s rRNA was performed. HBII-52 was elevated in several cancer specimens to levels not observed in any normal samples. On average HBII-52 was expressed higher in cancers (p=0.0711).
Figure 21:
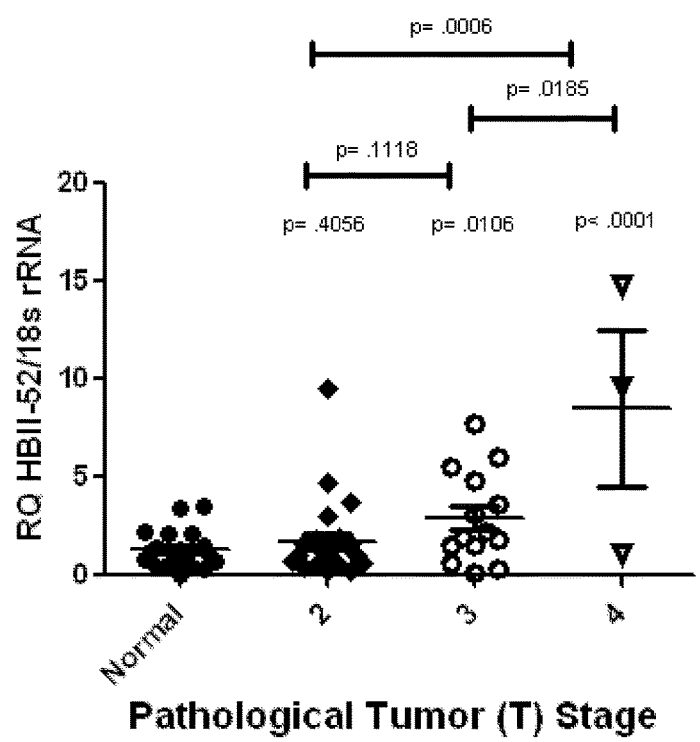
FIG. 21. HBII-52 expression is increased with increasing pathological tumor stage. Student's t-tests were performed to compare average expression levels of HBII-52 at various cancer stages to normal, as well as pair-wise comparisons between cancer stages. P-values directly above the data indicate the results of the statistical tests relative to normal sample average, while interstage comparisons are denoted by bars.
Figure 22:
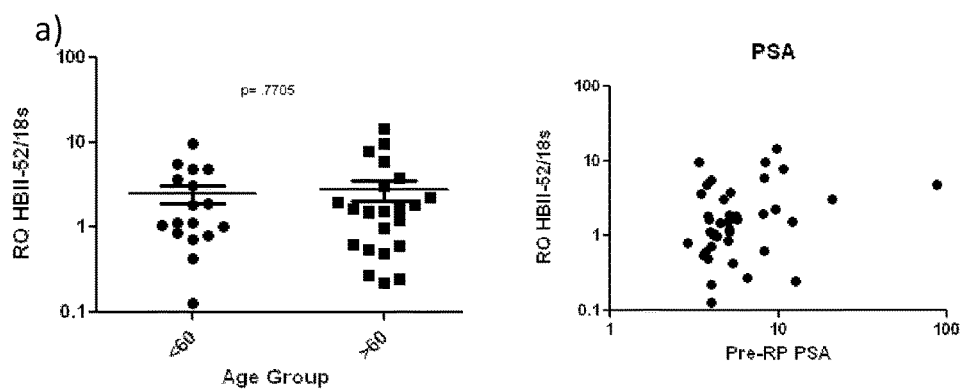
FIG. 22. HBII-52 expression does not correlate with age or PSA level. A) Student's t-tests were performed to compare average expression levels of HBII-52 between age groups and no significant difference was found. B) A spearman correlation was performed on recorded time-of-surgery PSA levels vs. HBII-52 in obtained specimens and no correlation was found, indicating HBII-52's utility as a marker independent of PSA.
Figure 23:
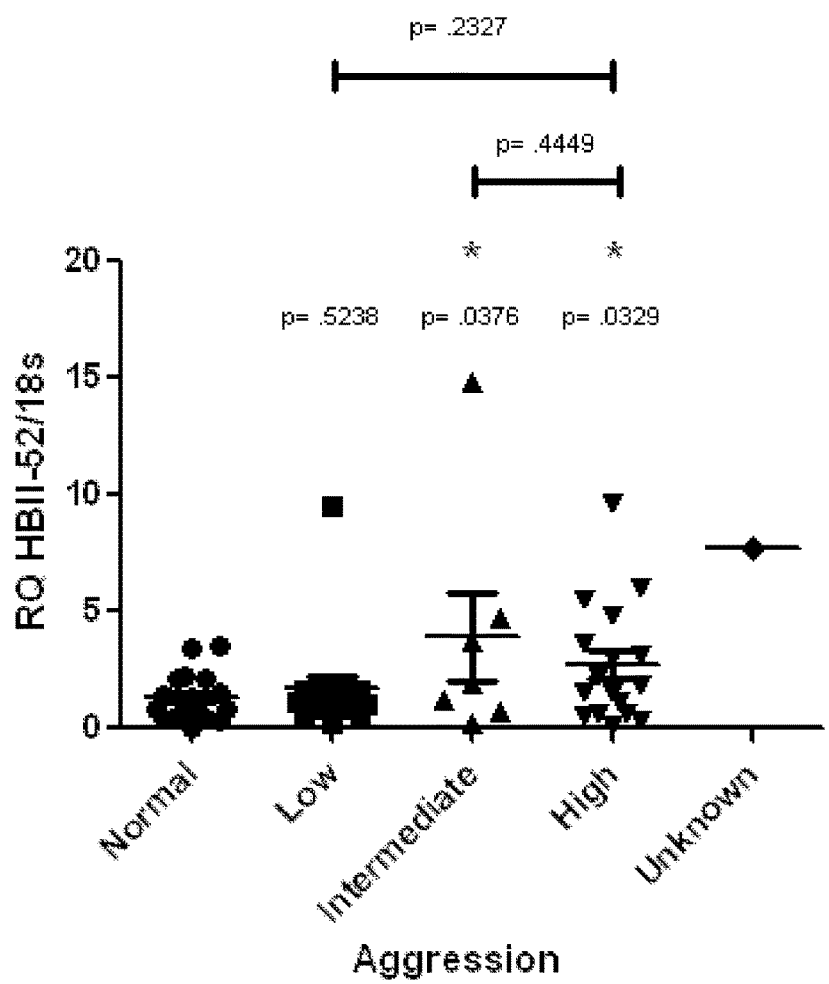
FIG. 23. HBII-52 expression is increased with increasing PCa Aggression. Highly aggressive disease is defined as Gleason sum 8, or PSA>20 ng/ml, or Gleason sum=7, and stage cT3-cT4. Non-aggressive (low) is defined as Gleason sum<7 and stage cT1-cT2, and PSA<10 ng/ml. Intermediate aggressive is defined as all other cases. These classifications are according to Shroeder, J C, et al. The Prostate, 2006.
Figure 24:
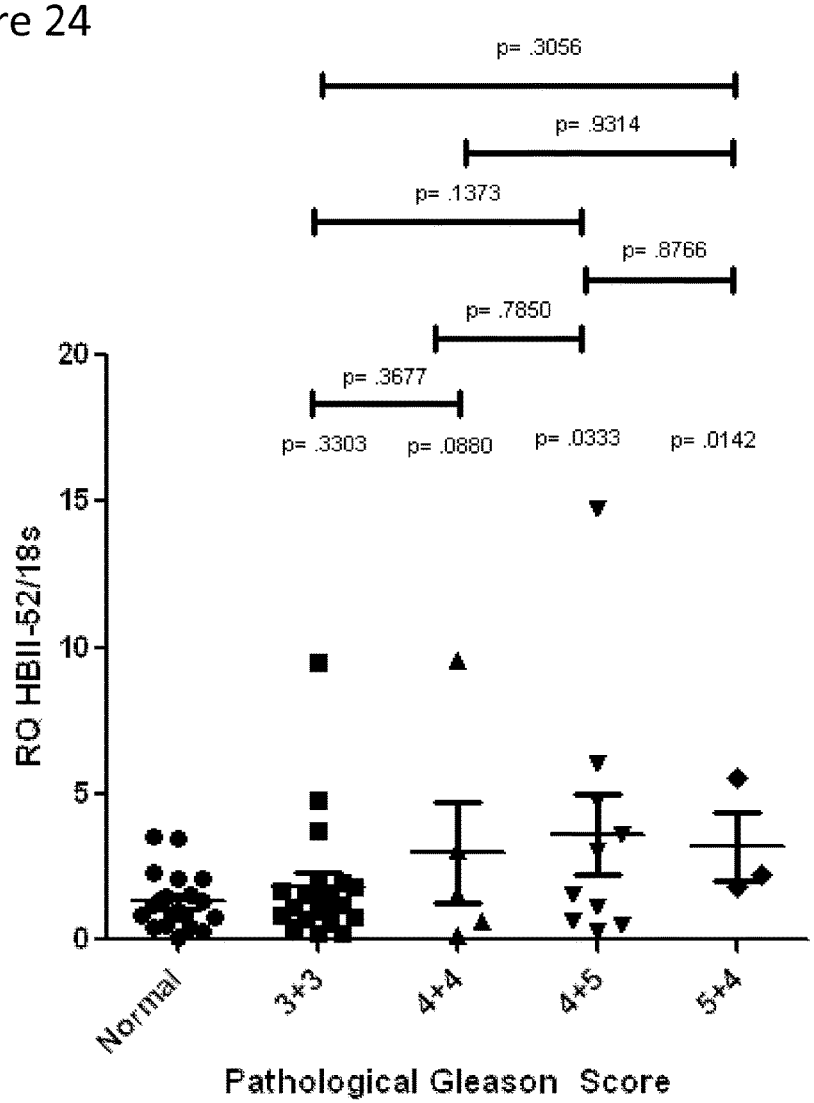
FIG. 24. HBII-52 expression is increased with increasing pathological Gleason score. Student's t-tests were performed to compare average expression levels of HBII-52 at various Gleason scores to normal, as well as pair-wise comparisons between Gleason score groupings. P-values directly above the data indicate the results of the statistical tests relative to normal sample average, while intergroup comparisons are denoted by bars.
Figure 25:
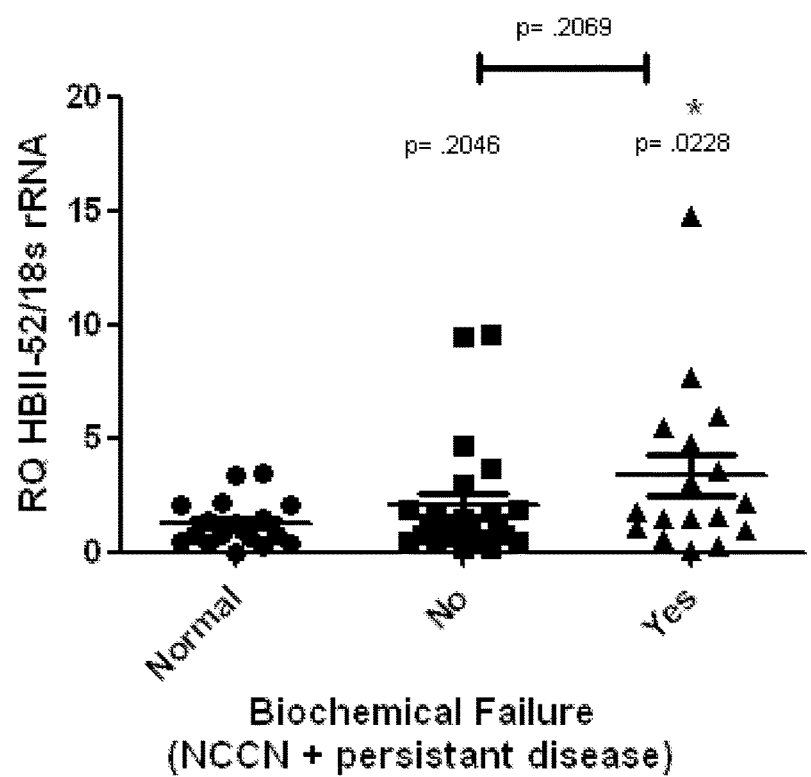
FIG. 25. HBII-52 expression is increased in patients that had biochemical failure. Student's t-tests were performed to compare average expression levels of HBII-52 at of failures and non-failures relative to normal, as well as a pair-wise comparison between cancer groups. P-values directly above the data indicate the results of the statistical tests relative to normal sample average, while the intergroup comparison is denoted by a bar. Biochemical Failure is defined as biochemical recurrence plus persistent disease (NCCN guidelines 2012). Biochemical Recurrence is defined as undetectable PSA after surgery with a subsequent detectable PSA level that increases on 2 or more subsequent measures. Persistent disease is defined as PSA levels that don't fall to undetectable levels after surgery. Also, PSA levels >0.03-<0.2 is persistent disease if also associated with adverse pathological factors (stage T3a or above, diffusely positive surgical margins) and >=0.2 PSA is also persistent disease.
Figure 26:
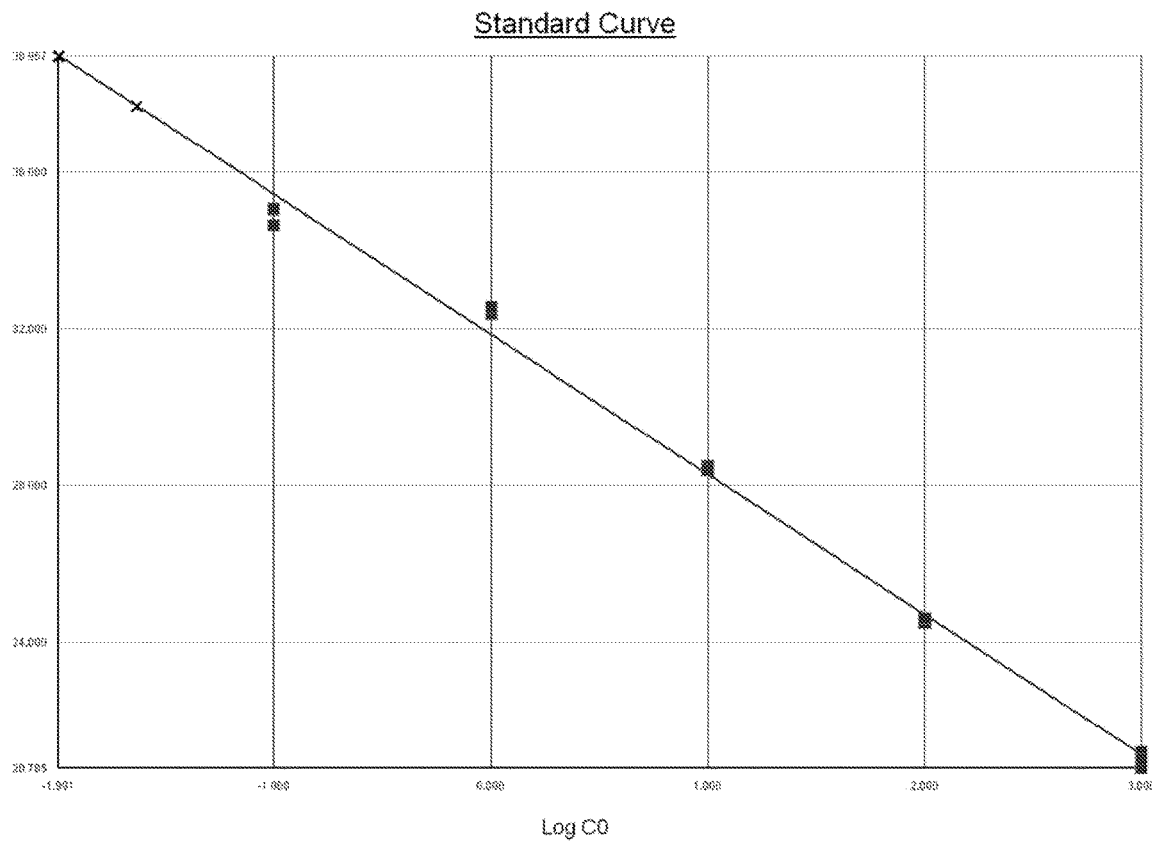
FIG. 26. Design and validation of mouse MBII-52 primers and probes for qPCR. Standard curves were generated from qPCR reactions from 1/10 serial dilutions of cDNA libraries generated from RNA isolated from mouse brain tissue. All qPCR experiments from cell lines and mouse tissue were conducted in 20 µL reaction volumes in 96-well format on an ABI 7300 real time PCR system. Each sample was aliquoted in triplicate into half skirt 96-well PCR plates, followed by primer/probe mixes and Taqman universal PCR mastermix, no AMPerase UNG, and then sealed with clear adhesive film. 40 cycles of standard protocol qPCR were run with annealing temperatures of 55° C. for HBII-52 and MBII-52, and 60° C. for all other primers. Gene expression was normalized using ΔΔCT method to an appropriate endogenous control as indicated

In certain specific embodiments, the primers depicted in FIG. 14 can be used in any of a variety of hybridization and/or polynucleotide amplification techniques to detect HBII-52. For example, in one embodiment, a multiplexed PCR-assay is developed to ascertain the presence of any of the polynucleotide sequences depicted in FIG. 13. In one embodiment, primers that can detect the consensus HBII-52 are used. Consistent with this, in an embodiment, the present disclosure includes a kit for detecting HBII-52. The kit can comprise any primers suitable for hybridizing to and/or amplifying HBII-52 in any type of assay that involves hybridization of an oligonucleotide, such as a primer for use in any type of polymerase chain reaction. In embodiments the kit comprises HBII-52 fwd: 5'-ATGAGAACCTTATAT-TGTCCTGAAG (SEQ ID NO:3) and HBII-52 rev: 5'-GGC-CTCAGCGTAATCCTA (SEQ ID NO:4). In an embodiment, the kit comprises HBII-52 probe: 5'-/56-FAM/GGTGATGACTTAAAAATCATGCTCAA/36-TAMSp/ (SEQ ID NO:5) for use in quantitative Reverse Transcription Polymerase Chain Reaction (qRT-PCR). In an embodiment, the kit comprises printed material which has directions for using the kit to analyze samples for the presence and/or absence of HBII-52 in a sample. In an embodiment, the instructions provide directions for using the primers to test for HBII-52 in a sample of prostate tissue from a subject suspected of having or diagnosed with prostate cancer. FIG. 14 also provides the sequence of one strand of an amplicon generated in an embodiment of the invention (ATGAGAAC-CTTATATTGTCCTGAAGAGAGGTGATGACT-TAAAAATCATGCT CAATAGGATTACGCTGAGGCCC (SEQ ID NO:6). Thus, in embodiments, this disclosure includes detecting an amplicon comprising one strand of DNA, wherein the strand of DNA comprises or consists of SEQ ID NO:6, and compositions comprising such amplicons and methods that involve forming such amplicons using primers described herein are included in the scope of the invention. The invention also provides kits comprising the primers in FIG. 14, or alternative or additional primers suitable for detecting HBII-52.

In certain aspects of the invention, detection of any one RNA equivalent of the sequences depicted in FIG. 13 is considered to also be detection of one or more or all of the RNA equivalents of the other polynucleotide sequences shown in FIG. 13.

With respect to snoRNAs, generally, they are stable and available in serum and are easily quantifiable by quantitative Reverse Transcription Polymerase Chain Reaction (qRT-PCR). HBII-52 has been mechanistically linked to 5-HT$_{2c}$R in human and mouse brain. HBII-52 affects 5-HT$_{2c}$R RNA editing and splicing, leading to the translation of the constitutively active isoform, 5-HT$_{2c\text{-}INI}$R. The importance of 5-HT$_{2c}$R signaling in prostate physiology or PCa is unknown.

Activation of 5-HT$_{2c}$R in an ectopic cellular environment can be transformative. For example, mouse embryonic fibroblasts (NIH 3T3 cells) expressing 5-HT$_{2c}$R form foci, which generate tumors when injected in mice. Together these data suggest 5-HT$_{2c}$R is a potential proto-oncogene. In the prostate, aberrant expression of HBII-52 could directly favor processing of pre-mRNA to 5-HT$_{2c\text{-}INI}$R, rendering tumors addicted to 5-HT$_{2c}$R pro-proliferative signals. Furthermore, this axis may be preferentially activated or selected for in brain or central nervous system (CNS) tumors, which originate in tissues that normally express HBII-52 or 5-HT$_{2c}$R. 5-HT$_{2c}$R signals directly to various downstream targets known to be intimately linked to cancer progression, including PCa, such as Erk and RhoA. Also, phosphatase and tensin homolog (Pten) is mutated or lost in the majority of PCa. Pten, when functional, can directly suppress 5-HT$_{2c}$R activity by dephosphorylating an intracellular residue and limiting coupling to G-proteins that mediate downstream signaling. Therefore, loss of Pten would favor activation of 5-HT$_{2c}$R. While the described molecules seem to play critical roles in PCa progression, targeted therapies, especially monotherapies have been less than successful due to feedback mechanisms that utilize alternative pathways to reinforce survival signals. Treatments with 5-HT$_{2c}$R inhibitors, alone or in combination with conventional chemotherapy, may be focused on a central signaling hub and could essentially deprive cancer cells of multiple pro-proliferative and survival signals.

Without intending to be constrained by theory, it is considered that the present disclosure will allow, in certain embodiments, physicians to reliably identify those patients that present a particular subset of poorly differentiated PCa that is unlikely to respond well to hormonal therapy and HBII-52 will classify a subset of brain/CNS tumors. In an embodiment, the disclosure includes testing a sample comprising prostate cancer tissue, detecting HBII-52, and stratifying the subject from which the sample was obtained as having a PCa that is unlikely to respond well to hormonal therapy.

HBII-52 belongs to a class of molecules, snoRNAs, whose function in cancer and potential use as blood-available biomarkers is understudied. Preliminary data including a gene expression microarray, retrospective tissue expression analysis in TRAMP PCa mouse model, prostate-specific Pten$^{-/-}$ mouse model, and in vitro studies in human and murine cell lines of both PCa and brain/CNS cancers support the notion that HBII-52 directly correlates with cancer progression and is expressed in numerous cancer cell lines of the prostate and brain. These data support our innovative approach of using HBII-52 to stratify PCa or other cancers by aggressiveness or differentiation state, or castration recurrent status, or to indicate therapy with 5-HT$_{2c}$R inhibitors.

Discussion of MBH-52/HBII-52 Expression and Non-Limiting Examples Demonstrating Embodiments of the Disclosure SnoRNAs are non-coding RNAs involved in RNA processing (1). There are two major subclasses of snoRNAs, termed box C/D and box H/ACA snoRNAs. These two classes contain characteristic guide sequences that are known to canonically pair with complementary regions on a target pre-rRNA, forming a RNA duplex and facilitating the enzymatic activity of methylases and uridylases that site specifically modify pre-rRNA bases by either 2'-O-methylation or pseudouridylation respectively. These modifications of the rRNA are critical to ribosome assembly and viability. In the last decade, various orphan snoRNAs have been identified that structurally resemble C/D box snoRNAs but do not contain sequence complementarity to rRNA. In fact, the snoRNA HBII-52 encoded by the SNORD115 gene has sequence complementarity to the pre-mRNA of 5-HT$_{2c}$R, enabling HBII-52 to target 5-HT$_{2c}$R pre-mRNA and affect critical RNA processing events (2). SnoRNA HBII-52 is encoded at chromosomal locus 15q11-13, a genomic region associated with complex regulation and implicated by genome-wide association studies in various diseases including cancer (3,4).

The role of non-coding RNAs (e.g. microRNAs, long non-coding RNAs, etc) in cancer is emerging as an important field. The role of snoRNAs in cancer, however, is a relatively understudied space. Like miRNAs and other nucleic acids known to exist cell-free, snoRNAs are available and stable in serum and plasma (5,6), making snoRNAs in general strong candidates for development as biomarkers. SnoRNAs also have very distinct functional consequences. Furthermore, snoRNAs can be differentially regulated and act as tumor suppressors and growth-arrest factors in cancer (7-11). Thus, snoRNAs are proving to be a robust and underexplored class of molecules in cellular regulation, with pathological consequences when deregulated.

HBII-52 is a snoRNA expressed almost exclusively in the brain from the SNORD115 gene on human chromosome locus 15q11-13. SNORD115 is conserved across several species (e.g. mouse, rat, human, dog). HBII-52 is found as 47 repeating copies that can be transcribed as one large transcript and processed into individual functional snoRNAs (13). Occasionally, a larger transcript having multiple copies of HBII-52 as well as other snoRNAs is transcribed (14). Specific histone methylation patterns dictate the epigenetic regulation of this region with the involvement of DNA methyl transferase 3a (DNMT3a), and DNA methyl transferase 1 (DNMT1) (4,15). In summary, locus 15q11-13 is a tightly regulated genomic region from which HBII-52 is normally exclusively expressed in brain and silenced elsewhere. Disruption of this regulatory network could lead to aberrant expression of HBII-52 in tissues where it is not normally expressed. Intriguingly, locus 15q11-13 has been implicated as a susceptibility locus for PCa in a number of Genome-Wide Association Studies (GWAS) of families and patients with hereditary (15q13-14)(16), late onset (15q11) (17) or aggressive (15q12)(18) PCa, including the largest study from The International Consortium for Prostate Cancer Genetics (ICPCG) that examined 1233 PCa pedigrees (18,19). Aberrant HBII-52 expression in PCa resulting from specific abnormalities at this locus may be one explanation for the PCa susceptibility findings. Cancer cells can amplify oncogenes to which they have become addicted for survival. This process, called oncogene amplification, is most notably observed in human epidermal growth factor receptor 2 (Her-2/neu) positive breast cancer (20). The tandemly repeated HBII-52 coding region seems to be primed for potential addiction, and this locus may be a proverbial on-off switch for concomitant expression of dozens of copies of the snoRNA from a single initial transcript.

Data presented herein from the TRAMP model implicate mouse ortholog MBII-52 as a significant player in late stage, poorly differentiated PCa and CR-PCa. Gene expression array analysis (Affymetrix) identified MBII-52 as having the greatest increase in expression amongst all probes on the array when comparing late stage palpable tumors to prostates of mice with early stage disease (data not shown). Follow-up, retrospective studies in TRAMP confirmed an increase in MBII-52 expression by qRT-PCR. Expression levels increased with disease progression with the highest expression observed in late stage, palpable tumors (FIG. 1). Furthermore, CR disease exhibited very high levels of MBII-52.

Figure 2:
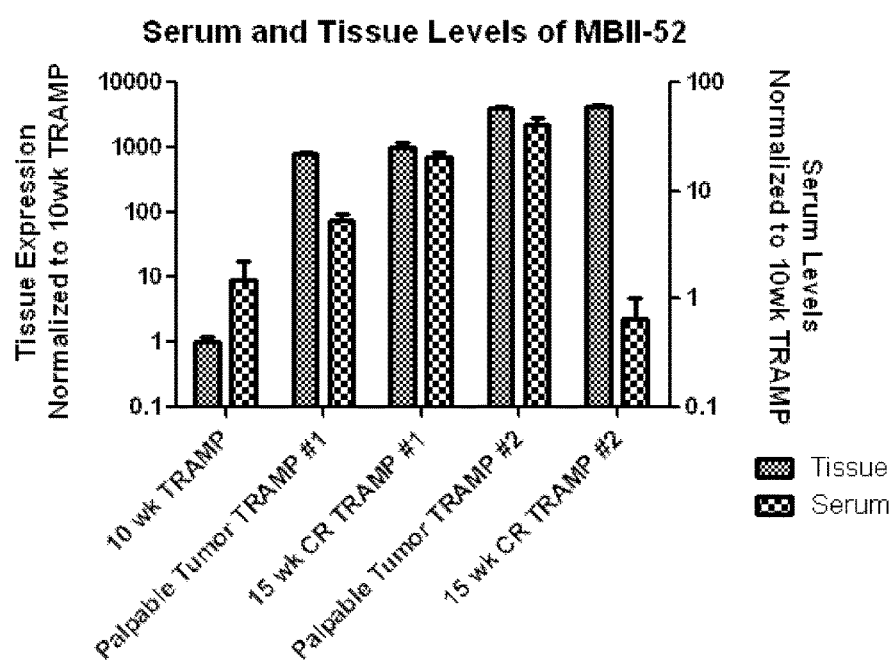
FIG. 2. Expression of MBII-52 in serum and matched prostate tissue samples from TRAMP mice. MBII-52 was readily amplified from serum by PCR. Expression in serum generally correlated with tissue expression.
Figure 3:
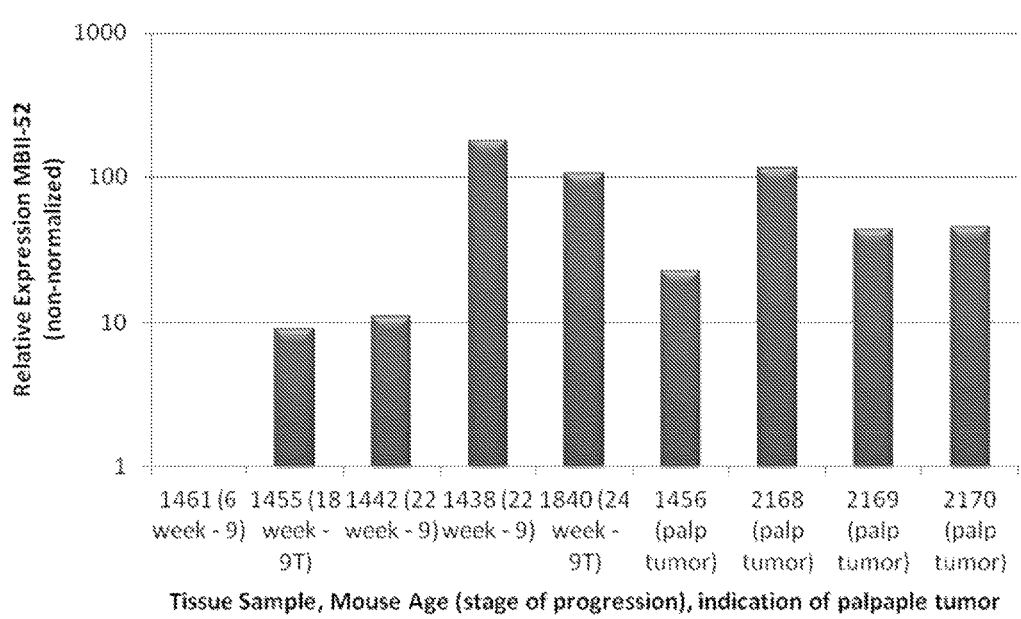
FIG. 3. Expression of MBII-52 in tissue samples from the prostate specific Pten$^{-/-}$ transgenic mouse model. MBII-52 appears to increase with severity of disease in the Pten$^{-/-}$ model FIG. 4. MB/HBII-52 is expressed in human prostate PCa cell lines. Tumorigenic RWPE2 expresses higher levels than non-tumorigenic RWPE1, in which HBII-52 is undetectable by qRT-PCR. LNCaP-C4-2 expresses higher levels than LNCaP. PC-3 expresses HBII-52 at moderate levels.

The pattern of expression of neuroendocrine (NE) biomarkers chromogranin A (CgA)(21) and dopa decarboxylase (DDC)(22,23) correlated with MBII-52 expression in TRAMP mice (FIG. 1), consistent with the noted NE differentiation (NED) in late stage TRAMP (24). This correlates MBII-52 with the emergence of NED. MBII-52 is serum-available in mice and easily detectable using standard RNA isolation (TRIzol, Invitrogen) and qRT-PCR protocols. In the same retrospective TRAMP study, serum levels generally correlate with prostate tissue RNA levels (FIG. 2), making MBII-52 potentially amenable to a highly sensitive, non-invasive, and cost-effective screening or diagnostic tool. RNA isolation from serum of TRAMP mice typically yields 200-400 ng of total RNA. Twenty microliters of mouse serum is sufficient to obtain these amounts and allow quantification of specific RNAs by qRT-PCR. MBII-52 expression was also evaluated in a small set of tumors and serum from prostate-specific Pten$^{-/-}$ mouse model and Hi-Myc model. Pten–/– mice also exhibited higher expression levels with progression, (FIG. 3).

Figure 4:
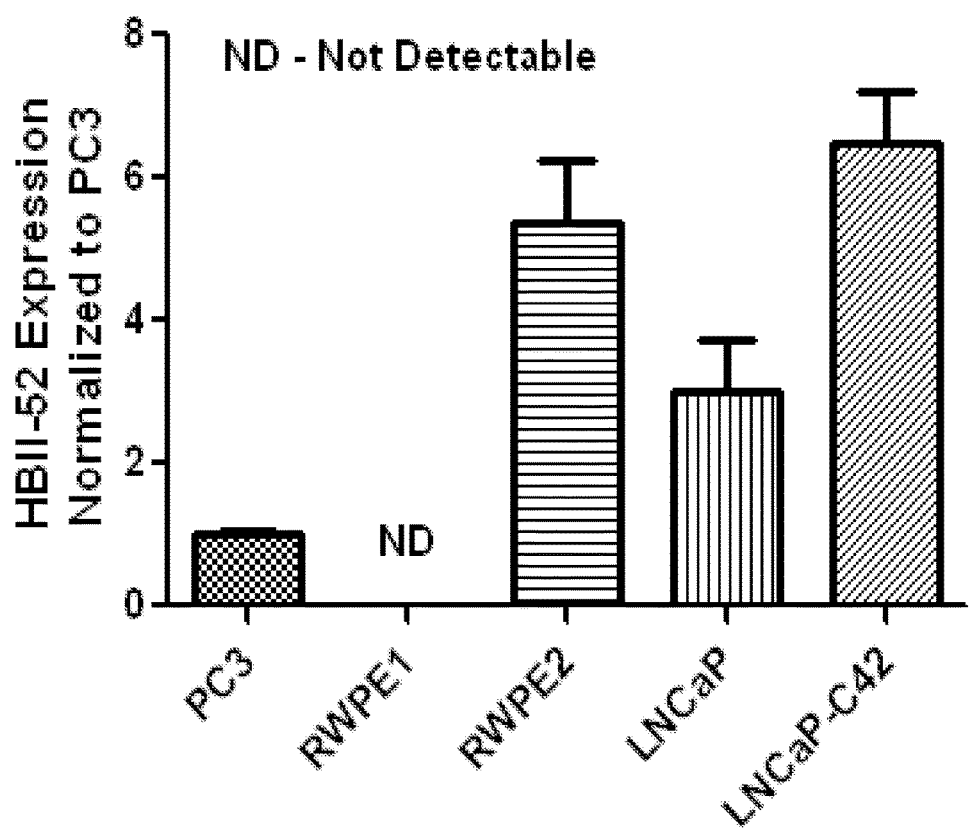
Figure 5:
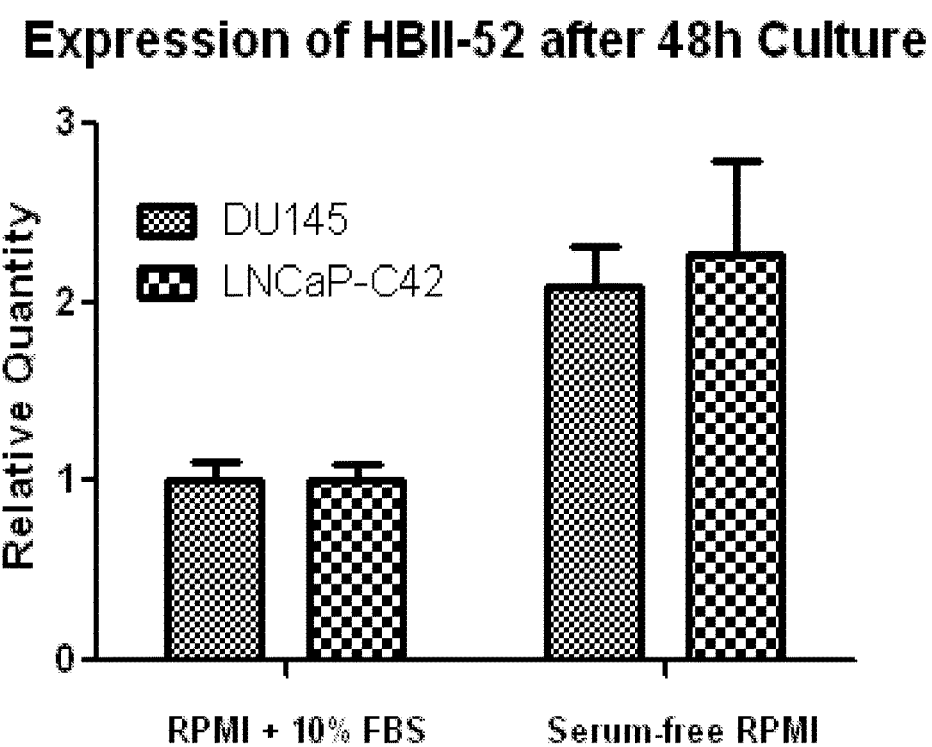
FIG. 5. Human homolog HBII-52 is induced by 48 h serum starvation. Induction of HBII-52 is also observed at 24 h and 72 h (data not shown).
Figure 6:
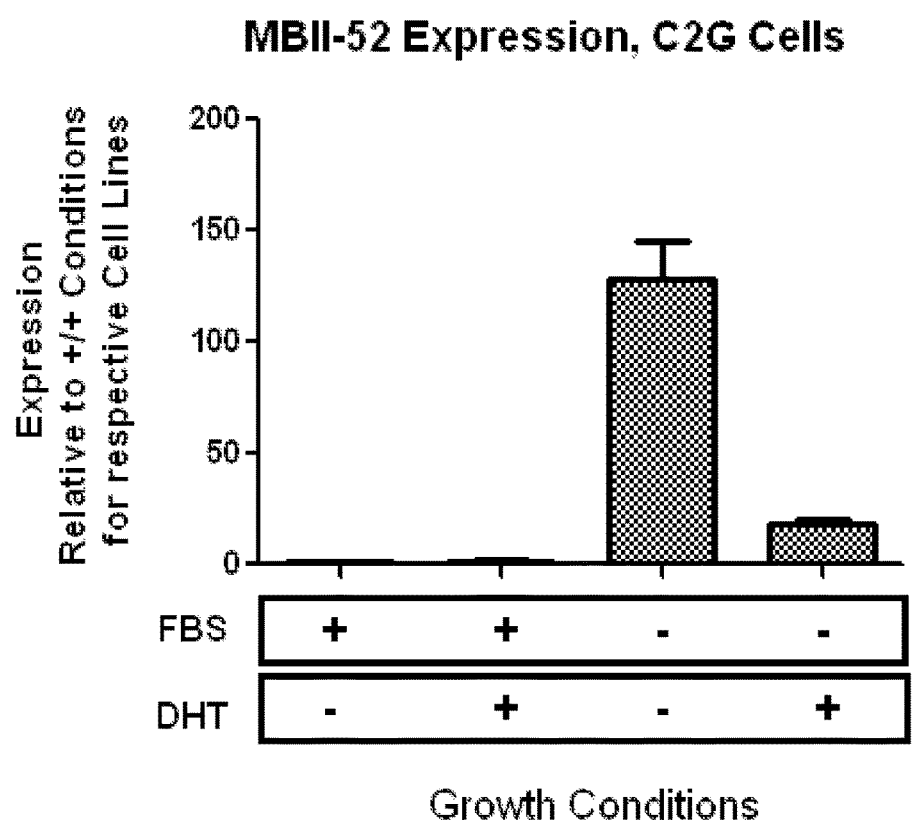
FIG. 6. In C2G cells, serum starvation for 72 h causes an increase in snoRNA expression by >100 fold. DHT supplementation in serum starved C2G cells appears to almost completely block the increase in MBII-52.

HBII-52 is undetected in non-tumorigenic human cells (RWPE1), and expressed at varying levels in PCa cell lines (LNCaP, LNCaP-C4-2, PC3, RWPE2) (FIG. 4). Serum starvation induces NED of PCa cell lines (25). Expression of HBII-52 increases with serum starvation, indicating that in cell culture, PCa cells upregulate HBII-52 when undergoing NED (FIG. 5). These data are consistent with our correlative observations in TRAMP. Furthermore, NED is associated with CR-PCa in vivo, supporting the importance of factors that induce NED as initiators of transition to androgen-independence (26). Increased expression after serum starvation also occurs in TRAMP cell lines, while addition of 5α-dihydrotestosterone (DHT) in the absence of serum abrogates the observed upregulation of MBII-52 (FIG. 6).

Figure 7:
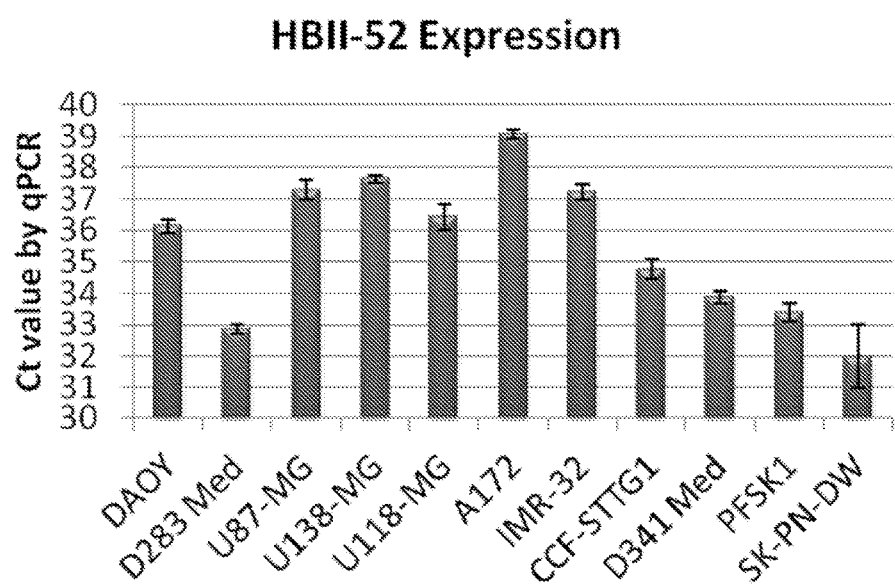
FIG. 7. Expression of HBII-52 in various brain/CNS tumor cell lines. Expression was measured from 3 successive RNA isolations. Data is represented as the average of 3 experiments with error bars indicate SEM.

HBII-52 expression was also evaluated in various human tumor cell lines for brain/CNS malignancies (Table 1) since this axis is known to be important for neuronal development. HBII-52 is variably expressed in these cell lines indicating it may be prevalent in some cancers and absent in others (FIG. 7). It's expression pattern in these cancer types may also be significant in terms of prognosis or therapeutic indication.

HBII-52 Affects 5-HT$_{2c}$R

HBII-52 exhibits partial or perfect sequence complementarity to multiple mRNA targets (27). Of the predicted targets by in silico sequence alignments, one lead that has been validated experimentally is the serotonin 2c receptor, 5-HT$_{2c}$R. There is an 18-nucleotide perfectly complementary region between the human snoRNA HBII-52 and 5-HT$_{2c}$R pre-mRNA. The interaction of the two RNAs has been experimentally validated with HBII-52 affecting editing and splice-site selection of the pre-mRNA (2). Specifically, HBII-52 reduces A-to-I RNA editing at five specific adenosine nucleotides in the pre-mRNA of 5-HT$_{2c}$R and facilitates proper splicing to a processed isoform that is more responsive to 5-HT and also has constitutive (ligand-independent) activity.

We propose that once overexpressed in an atypical environment, such as the prostate, snoRNA HBII-52 exerts its oncogenic function by affecting RNA editing and splicing of its mRNA target, 5-HT$_{2c}$R. RNA editing is a process in which pre-mRNA adenosines are chemically modified to inosines by adenosine deaminase targeting RNA enzymes (ADARs) (28). Inosines are effectively read by the ribosome as guanosines, therefore A-to-I editing results in multiple amino acid sequences from a single pre-mRNA transcript, adding an additional level of complexity and regulation to the proteome. RNA editing may allow organisms to respond to environmental stresses in order to evolve and adapt to a selective pressure, as has been demonstrated in Octopus ion-gated channels (29). This adaptability due to RNA editing may similarly allow specific responses to selective pressures in cancer. Thus, RNA editing is an important regulatory mechanism, and deregulation of proper RNA-editing could specifically influence normal cell regulatory events and play a significant role in disease processes.

TABLE 1

Human brain/CNS tumor cell lines evaluated for HBII-52 and 5HT$_{2c}$R expression

| Cell Line | Source | Type | Tumorigenic |
|---|---|---|---|
| Daoy | 4 year old male | medulloblastoma | Yes |
| D283 Med | 6 year old male | medulloblastoma | Yes |
| U-87 MG | 44 year old male | glioblastoma | Yes |
| U-138 MG | 47 year old male | glioblastoma | No |
| CCF-STTG1 | 68 year old female | astrocytoma | Unknown |
| D341 Med | 3.5 year old male | medulloblastoma | Yes |
| PFSK-1 | 22 month old male | PNET | Yes |
| SK-PN-DW | 17 year old male | neuroblastoma | Yes |
| U-118 MG | 50 year old male | glioblastoma | Yes |
| A-172 | 53 year old male | glioblastoma | No |
| IMR-32 | 13 month old male | neuroblastoma | Unknown |

RNA splicing adds an additional level of post-transcriptional regulation in cells. Protein coding genes are first transcribed from DNA to pre-mRNA containing introns and exons. The pre-mRNA is spliced into a processed mRNA that encodes for and can be translated by the ribosomal machinery into a protein. As many as 95% of multi-exon genes and at least 86% of all human genes, are predicted to yield alternative splice forms (30). The existence of alternative splicing greatly increases the diversity of the proteome, and adds an additional level of complexity to gene regulation including tissue specific expression. Alternative splicing events can be ubiquitous or occur specifically in response to developmental/physiological cues (31). Deregulation of splicing can be pathogenic and has been implicated in a variety of human diseases including cancer (32,33). The most convincing and striking evidence that alternative splicing plays an important and perhaps fundamental role in cancer progression is that a large majority of genes encoding for proteins with roles in apoptosis give rise to both pro- and anti-apoptotic isoforms processed from the same pre-mRNA as a result of alternative splicing (34). A single aberrant splicing event can instantly turn a tumor suppressor into a tumor promoter. Mis-splicing events can affect many pathways that contribute to cancer progression, beyond the discussed examples in apoptosis and metastasis. For example, metabolism, cell cycle control, invasiveness, and angiogenesis are affected by RNA splicing events (reviewed in (33)). Many splice variants implicated in cancer are expressed during growth and development, are "turned off" in adult cells, and are re-expressed in cancer. 5-HT$_{2c}$R splicing is affected by HBII-52, and this process may be critical for progression of a specific subset of cancers.

Figure 8:
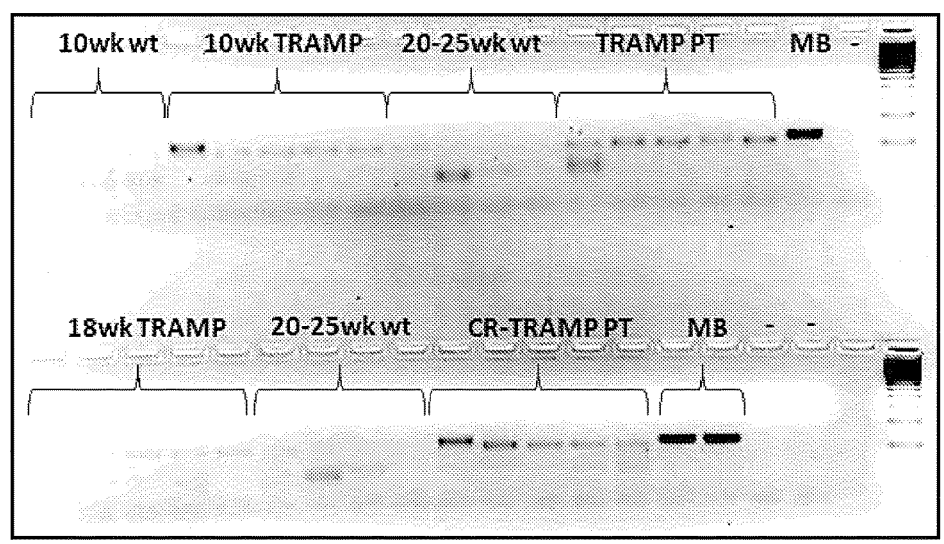
FIG. 8. $5HT_{2c\text{-}INI}R$ was detected using PCR primers specifically designed to anneal to the multiple editing site in the pre-mRNA isolated from TRAMP tumors or wildtype mouse prostate tissue. Mouse brain is a positive control. Ladder is 100 bp ladder.

The 5-HT$_{2c}$R pre-mRNA contains five adenosines (termed A, B, C, C', and D) that are subject to A-to-I editing by ADAR. Since inosines are read by the translational machinery as if they were guanosines (28), different edited permutations result in different amino acids in the final translated protein. These permutations involve alterations of three codons, and resulting isoforms are denoted by a three letter nomenclature describing the amino acid sequence. Fourteen products arise in humans ranging from the completely unedited (INI) to the fully edited (VGV) isoforms (35). Editing provides precise control over the regulatory network controlled by this receptor class. Differences in the signaling cascade and activity of 5-HT$_{2c-INI}$R and 5-HT$_{2c-VGV}$R are drastic (35-37). Furthermore, 3 of the 5 edit sites in the 5-HT$_{2c}$R pre-mRNA are located within a putative splice-silencing site (38). In the absence of HBII-52 and when unedited, the splice-silencing site causes the pre-mRNA to be alternatively spliced, generating a premature stop codon resulting in a truncated, non-functional protein that lacks an intracellular loop critical for G-protein binding. Editing at these ADAR target sites modifies the splice-silencer, therefore permitting proper splicing to the full length receptor. However, the change in amino acid sequence due to editing results in a receptor with 10-100-fold reduced activity (37). HBII-52 can also contribute to this complex process by annealing to the 5-HT$_{2c}$R pre-mRNA at the site of editing and splice-site selection. In the presence of HBII-52, editing is significantly reduced, and proper splicing is permitted. Therefore, in the presence of HBII-52, a full-length, less-edited or unedited transcript is available for translation (2,38). It was observed that expression of 5-HT$_{2c-INI}$R in TRAMP tumors correlated with expression of MBII-52. Namely, 5-HT$_{2c-INI}$R was elevated in late-stage poorly differentiated tumors and CR tumors relative to prostates from control wildtype mice (FIG. 8). Mouse brain tissue was used as a positive control for 5-HT$_{2c-INI}$R expression. The receptor that results from unedited HBII-52-mediated splicing is substantially more active, and therefore in the presence of HBII-52, one expects a more prominent signaling axis via 5-HT$_{2c}$R. 5-HT$_{2c-INI}$R was detected using PCR primers specifically designed to anneal to the multiple editing site in the pre-mRNA so that they would only amplify completely unedited or near unedited (constitutively active) isoforms of the receptor.

Figure 9:
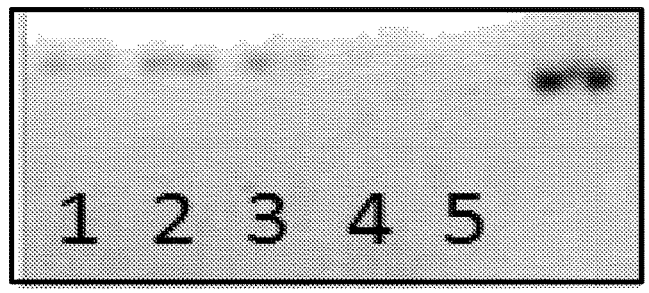
FIG. 9. In TRAMP C2G cell lines with stable MBII-52 expression, $5HT_{2c\text{-}INI}R$ levels were increased relative to controls. C2D. 100 bp molecular marker is shown to the right of lane 5.

To test the hypothesis that HB/MBII-52 can activate 5-HT$_{2c}$R and promote cancer progression stable cell lines were generated from TRAMP C2D and C2G cells that overexpress MBII-52 from pSilencer 4.1 CMV vector along with control cells expressing a scrambled RNA that has no homology to the mouse or human genome. MBII-52 was overexpressed ~70-fold in C2G stable cell lines resulting in increased levels of 5-HT$_{2c-INI}$R, however, C2D cells which failed to adequately overexpress MBII-52 (only 4-fold overexpression of the RNA) did not influence 5-HT$_{2c-INI}$R levels (FIG. 9).

As the 5-HT$_{2c}$R pre-mRNA is edited, there is a decrease in both agonist-independent signaling (constitutive activity) and affinity for agonists (e.g. serotonin, 5-HT). The fully edited isoform (VGV) is completely dependent on 5-HT binding and is the least active of all isoforms while the entirely unedited isoform (INI) is the most active form and is constitutively active and acts entirely independent of ligand binding (35). Downstream signaling by 5-HT$_{2c}$R can be blocked or reversed by antagonists or inverse agonists (35,36).

Figure 10:
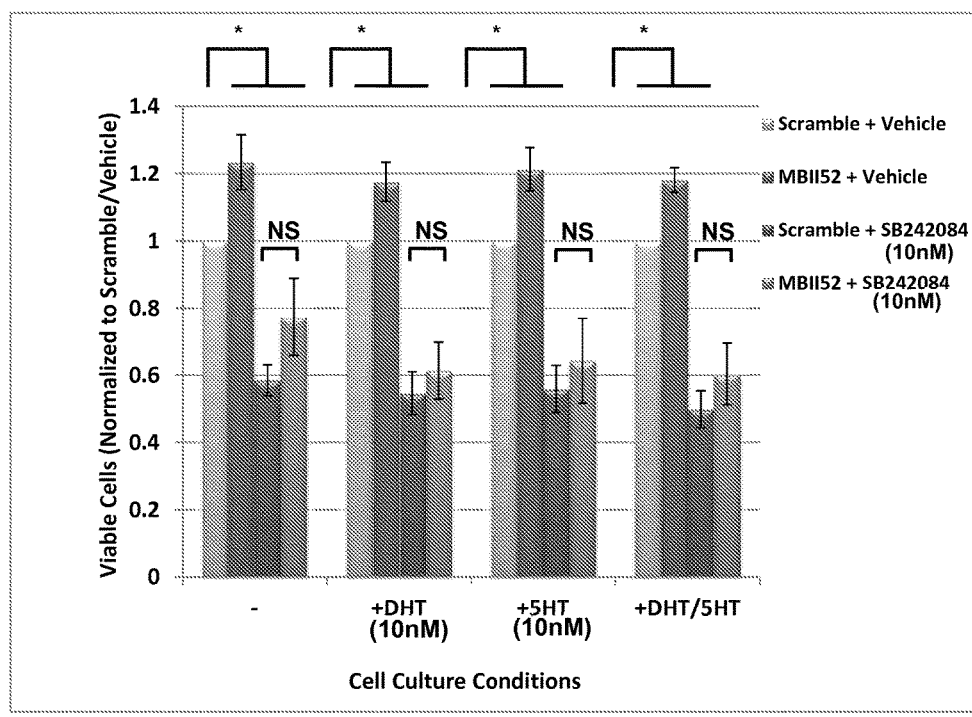
FIG. 10. MBII-52 was stably overexpressed (>60-fold overexpression) in TRAMP-C2G cells from the pSilencer CMV 4.1 vector. Cell viability was measured (n=5, error bars are SEM) after 72 h culture using Cell-Titer Fluor cell viability assay and normalized to scramble-transfected, vehicle-treated control. One-sample t-tests were performed to compare experimental groups with scramble/vehicle control. Two-tailed t-tests were used to compare the two SB 242,084 treatment groups with each other. * indicated p<0.05 for either test. MBII-52 increases cell viability, while SB 242,084 inhibits it. Neither DHT nor 5-HT appear to have much influence on the effect of MBII-52 or SB 242,084

Numerous downstream pathways activated by 5-HT$_{2c}$R have been studied in neuronal cell lines with a focus on neurological development and disease. The pathways relevant to this disclosure are Erk, PI3-K/Akt and RhoA (36,39). Each has previously been studied and targeted in PCa and other cancers. Activation of these pathways during PCa progression or in vitro can directly propagate a transition to malignancy. For example, Erk upregulates hypoxia inducible factor 1 alpha (HIF1α) and therefore vascular endothelial growth factor (Vegf) in response to hypoxia in rats (40). Vegf secretion also appears to be regulated by Erk in LNCaP cell lines (41). Erk is also able to transactivate the androgen receptor (AR) independent of androgen, by phosphorylating steroid receptor co-activator-1 (SRC-1), which then binds AR resulting in ligand-independent activation of AR. Therefore, Erk directly contributes to androgen-independence (41). PI3-K/Akt is involved in cell proliferation and apoptosis (42). RhoA activation causes increased invasiveness (43) and it has also been linked to androgen action in PCa (44). It was therefore expected that overexpression of MBII-52 would result in a constitutively active 5-$HT_{2c}R$ would contribute to cell proliferation by activating these pathways independent of androgens (e.g. DHT) or 5-HT. Indeed, stable cell lines overexpressing MBII-52 appeared more proliferative then scramble control stable cell lines in a 72 h growth assay, after which viability was measured using Cell-Titer Fluor Assay (n=5) (FIG. 10). SB 242,084 inhibition was effective in both scramble and MBII-52 overexpressing cells, however, MBII-52 overexpressing cells did not appear to be "addicted" to MBII-52 as inhibition was not more effective in this particular model system.

HBII-52 and 5-$HT_{2c}R$ are normally expressed in the brain and are critical for neurological development. Dysregulation of the pathways that they control may therefore contribute to malignancy in the brain or CNS. Brain/CNS and neuroblastoma tumors are cancers of the nervous system and may have similar molecular etiologies and include a broad category of tumors arising from numerous cell types in the CNS (45). The most prevalent forms of brain tumors are gliomas and primitive neuroectodermal tumors (PNETs) (46,47). Glioma is a broad category referring to tumors arising from glial cells in the CNS, and can include astrocytomas, oligodendrogliomas, and ependymomas. Brain/CNS tumors have varying degrees of aggressiveness. Low-grade gliomas are relatively benign with 5-year survival rates greater than 85%. However, 5-year survival rates for intermediate (anaplastic astrocytoma) and high-grade gliomas (glioblastoma) are 35 and 20% respectively (47,48). PNETs have a 60% 5-year disease free survival rate. Overall, poor clinical outcome in the more aggressive forms of brain/CNS tumors demonstrate a need for new therapeutic approaches.

5-HT is an important signaling molecule in the nervous system, responsible for mediating a number of downstream effector pathways through activation of a variety of 5-HT receptor family members (49). Human fetal astrocytes and glioma cell lines express a wide range of serotonin receptors, and are stimulated to proliferate and migrate by 5-HT (50). 5-$HT_{2c}R$ is highly expressed in choroid plexus tumors, a form of pediatric brain/CNS tumor, demonstrating a possible role in clinically relevant disease (51). Also, the pre-mRNA for 5-$HT_{2c}R$ can be alternatively edited and spliced in gliomas (52). It is likely that expression of HBII-52 results in processing of a constitutively active isoform of 5-$HT_{2c}R$ that contributes to, or drives progression of certain brain/CNS tumors or neuroblastomas. Furthermore, neuronal tumors may be particularly vulnerable to oncogenic transformation by HBII-52 since CNS tissues express the serotonin receptor.

Preclinical Efficacy of 5-$HT_{2c}R$ Inhibition

Constitutively active 5-$HT_{2c\text{-}INI}R$, which is preferentially and aberrantly expressed in the presence of HBII-52, acts upstream of and signals directly and constitutively to several targets that contribute to cancer progression (36, 39, 53, 54). It is possible that, 5-$HT_{2c\text{-}INI}R$ acts as the upstream hub/node for many signaling networks during cancer progression. Thus, 5-$HT_{2c\text{-}INI}R$ is a logical and promising therapeutic target in brain and prostate cancer. Furthermore, Pten and is a tumor suppressor that interacts with 5-$HT_{2c}R$ and regulates the phosphorylation status of the intracellular loops on 5-$HT_{2c\text{-}INI}R$, thereby affecting coupling to G-proteins and the resulting downstream signaling events (55). Loss of a copy of Pten is extremely common in advanced PCa (~60% of cases) and other cancers as well (56). Deregulation of Pten results in an increased activation of the PI3-K/Akt pathway, a pathway that is directly activated by 5-$HT_{2c\text{-}INI}R$. Mutation or loss of Pten correlates with "hormone-independent" PCa (57). Therefore, the tumor suppressive role of Pten in the prostate may be, in part, also mediated via regulation or suppression of 5-$HT_{2c}R$ signaling. 5-$HT_{2c}R$ has been extensively explored as a drug target in neurological disorders such as schizophrenia, anxiety, and epilepsy among others (reviewed in (35)). Also, agonism of 5-$HT_{2c}R$ has been pursued as a therapeutic modality for obesity and diabetes (58). However, neither HBII-52 nor 5-$HT_{2c}R$ have been pursued as significant contributors to PCa or as therapeutic targets. Therefore, validation of HBII-52 as a functional biomarker, and the consequence of its expression: 5-$HT_{2c\text{-}INI}R$, as a target in a variety of cancers, including but not necessarily PCa and brain cancer, are both novel propositions.

The G-Protein Coupled receptor (GPCR), 5-$HT_{2c}R$ may be a central node able to signal directly to multiple oncogenic pathways described herein, utilizing these pathways upon androgen deprivation or otherwise during disease progression. Fortuitously, GPCRs are the most drugable class of molecules in the entire genome. This is exemplified by the fact that >50% of currently approved therapeutic agents target GPCRs (59,60). GPCRs can act as oncogenes. For instance, GPCRs can obtain mutations activating them, or constitutively active GPCRs can be virally introduced into cells. Even endogenous GPCRs without mutations can be oncogenic by activation of the receptor by endogenous ligand released from nearby tumor or stromal cells (59). In fact, 5-$HT_{2c}R$ (formerly denoted 5-$HT_{1c}R$) is a GPCR that can transform cells, acting as a proto-oncogene with transforming capability in mouse (61) but not hamster fibroblasts (62). Endogenous ligand, 5-HT, is known to exert growth promoting effects in PCa cell lines. Other 5-HT receptors (e.g. 5-$HT_{1a}R$, 5-$HT_{1b}R$) have been targeted in pre-clinical studies with moderate or sometimes no efficacy (63-65). We hypothesize that the growth promoting effect of 5-HT is likely mediated in part via 5-$HT_{2c}R$. Prolonged exposure to endogenous ligand, however, both in vivo and in vitro causes a direct feedback loop that downregulates constitutive, highly active isoforms of 5-$HT_{2c}R$ in favor of less active, edited isoforms in order to desensitize cells to 5-HT (66,67). There is clearly a complex interplay between the growth promoting effects of 5-HT and feedback regulation of 5-$HT_{2c}R$ and its isoforms by RNA editing or splicing, which is influenced by HBII-52. Malfunction of the tightly controlled regulation of 5-$HT_{2c}R$ and its target pathways by aberrant overexpression of HBII-52 would be devastating to normal cell regulation and cause hyperactivation of the known pathways described, many of which are oncogenic. The proposed mechanistic link connecting HBII-52, 5-$HT_{2c\text{-}INI}R$ and downstream targets including Erk and RhoA amongst others is novel in the context of cancer including PCa and brain tumors, and may specifically provide new insight into CR-PCa and the factors involved in progression of PCa to an aggressive, poorly differentiated state.

All of this evidence points to 5-$HT_{2c}R$ as a valid and novel therapeutic target for cancer. HBII-52 and 5-$HT_{2c}R$ may be particularly important in brain tumors or prostate tumors with the NE phenotype (SCC/NED PCa). NED alone has been studied as a determinant of transition from "androgen-dependant" to "androgen-independent" or aggressive disease. NED is associated with poor prognosis, late stage and CR-PCa (26, 68, 69). NED is potentially causative of CR-PCa and also correlates with disease aggressiveness (68,70). Chromogranin A (CgA) has been used as a biomarker in both serum and tissue to identify NE populations and predict survival and hormone-refractory status. However, amongst the limitations of CgA is that while CgA can stratify PCa patients for prognoses, CgA is present at comparable levels in healthy patients (69), and thus has limited utility as a screening tool. The mechanisms by which prostate tumors acquire NE properties are poorly understood, although some have shown that activation of the Erk pathway can directly cause a transition of LNCaP cells into a NE-like state (71,72). Therefore, downstream pathways have been shown in vitro to play an integral role in the transition from "androgen dependence" to an "androgen-independent", NE phenotype.

Selective and potent antagonists and inverse agonists against 5-HT$_{2c}$R are commercially available. In 1997, synthesis of a 5-HT$_{2c}$R specific antagonist, SB 242,084 was first reported (73). SB 242,084 was an improvement over the earlier generation inhibitor, SB 206,553, in that it was more resistant to the metabolic methylation than SB206,553. Furthermore, SB242,084 has increased potency and greater than 100-fold selectivity for 5-HT$_{2c}$R receptor over 5-HT$_{2a}$R and 5-HT$_{2b}$R (73). SB242,084 exhibits potent antagonist activity in vitro and in vivo (73,74) and is readily synthesized by a longest linear sequence of four steps from commercially available starting materials.

SB 242,084 affects receptor internalization and inhibits activation of downstream targets including Erk (36,75). SB 242,084 has been explored in pre-clinical studies as a therapeutic modality in schizophrenia and other neurological disorders (35). SB 242,084 is a promising lead compound. In this disclosure SB 242,084 and SB 206,553 are examined in pre-clinical studies for the treatment of brain tumors, and poorly differentiated or CR-PCa.

Figure 11:
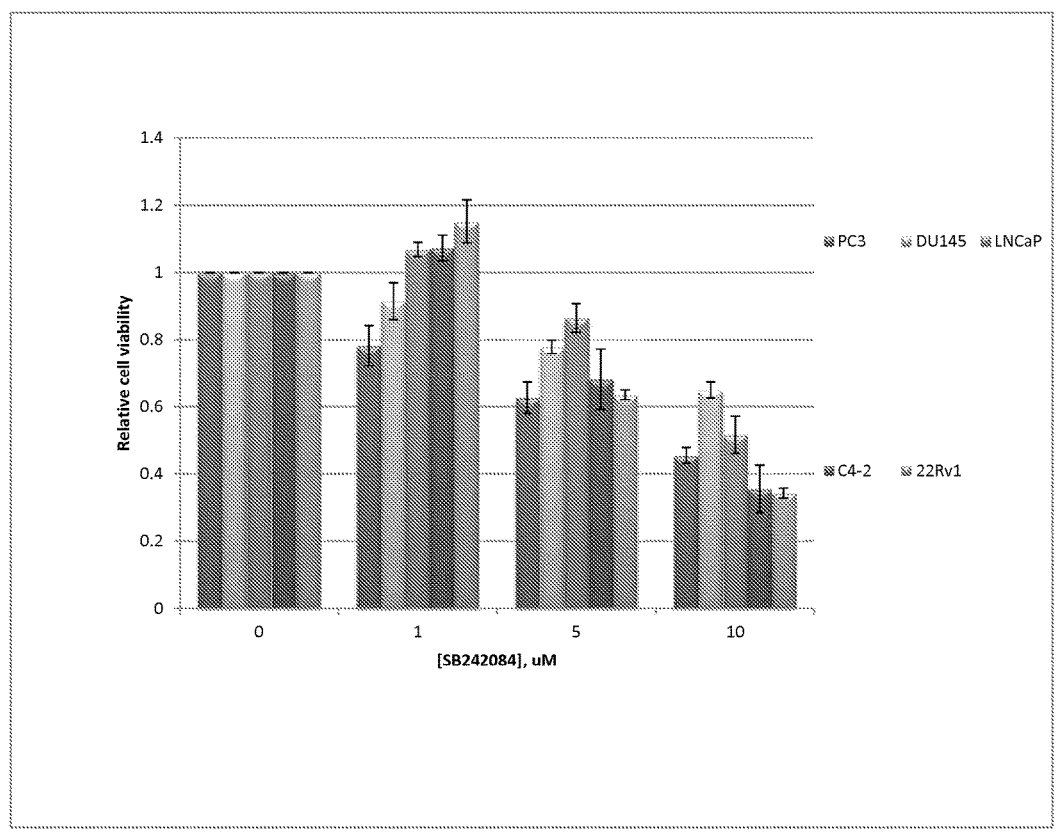
FIG. 11. Human Prostate cancer cell lines were treated with SB 242,084 for 72 h. A dose-dependent decrease in cell viability levels was observed. Data is the average of 3 independent experiments with error bars indicating SEM.
Figure 12:
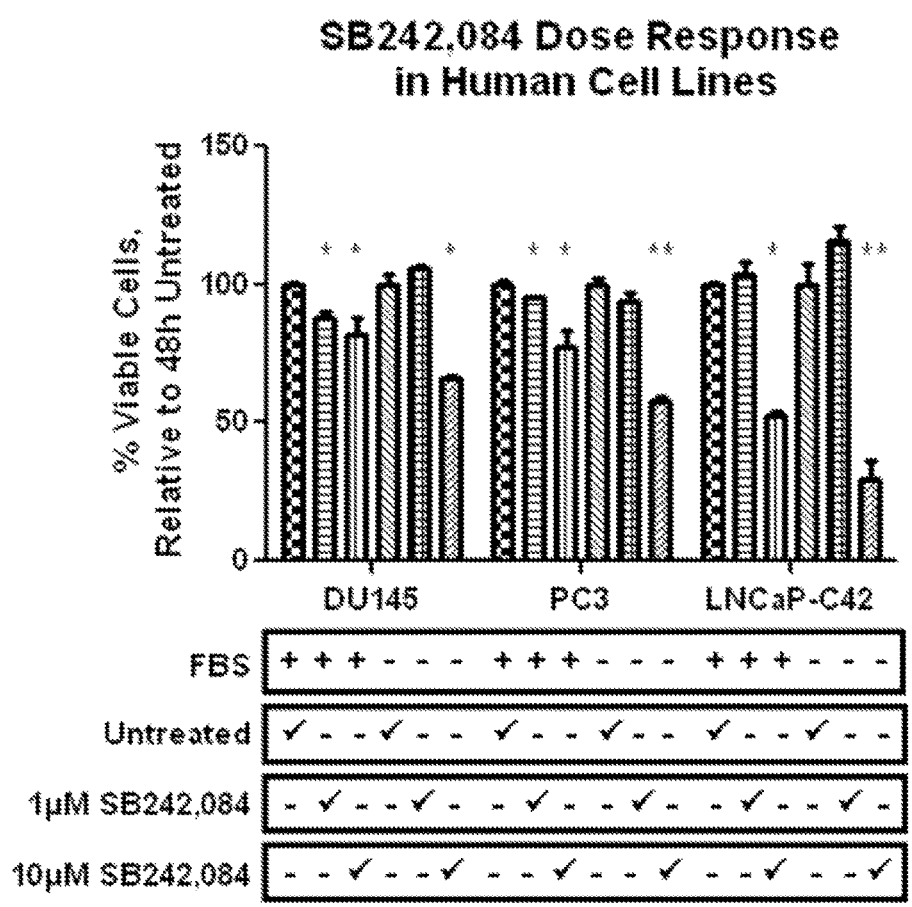
FIG. 12. Growth Inhibition in various human PCa cell lines is significantly improved (* indicates p<0.05 by student t-test) upon serum starvation. Data is representative of multiple independent experiments.

Our tests indicate that SB 242,084 is growth-inhibitory in human PCa cell lines (FIG. 11). The effect of SB242,084 was significantly (p<0.05) further improved under serum starvation in both PC3 and LNCaP-C4-2 cells (FIG. 12). Recalling that serum starvation induces NED in these cells and causes upregulation of HBII-52, these data indicate that SB 242,084 is most effective when NE phenotype is present. Collectively, these data point to a promising therapeutic candidate in PCa and cancers expressing HBII-52/5-HT$_{2c}$R.

FIGS. 15-26 show: the expression of MBII-52 in various PCa transgenic mouse models; HBII-52 overexpression in human PCa cell line DU145; overexpression of HBII-52 affects cell viability in response to 5-HT treatment; induction of HBII-52 expression in a medulloblastoma cell line results in Erk Activation; a summary of clinical samples and associated data utilized for evaluation of HBII-52 expression from clinical specimens; HBII-52 expression is elevated in human clinical PCa samples; qRT-PCR for HBII-52 and 18s was performed and HBII-52 was elevated in several cancer specimens to levels not observed in any normal samples; HBII-52 expression is increased with increasing pathological tumor stage; HBII-52 expression does not appear to correlate with age or PSA level; HBII-52 expression is increased with increasing PCa aggression; HBII-52 expression is increased with increasing pathological Gleason score; and HBII-52 expression is increased in patients that had biochemical failure.

REFERENCES

1. Bachellerie, J. P., Cavaille, J., and Huttenhofer, A. (2002) Biochimie 84, 775-790
2. Kishore, S., and Stamm, S. (2006) Science 311, 230-232
3. Hogart, A., Leung, K. N., Wang, N. J., Wu, D. J., Driscoll, J., Vallero, R. O., Schanen, N. C., and LaSalle, J. M. (2009) J Med Genet 46, 86-93
4. Chamberlain, S. J., and Lalande, M. (2010) Neurobiol Dis 39, 13-20
5. Schwarzenbach, H., Hoon, D. S., and Pantel, K. (2011) Nat Rev Cancer 11, 426-437
6. Liao, J., Yu, L., Mei, Y., Guarnera, M., Shen, J., Li, R., Liu, Z., and Jiang, F. (2010) Mol Cancer 9, 198
7. Dong, X. Y., Guo, P., Boyd, J., Sun, X., Li, Q., Zhou, W., and Dong, J. T. (2009) J Genet Genomics 36, 447-454
8. Mourtada-Maarabouni, M., Pickard, M. R., Hedge, V. L., Farzaneh, F., and Williams, G. T. (2009) Oncogene 28, 195-208
9. Chang, L. S., Lin, S. Y., Lieu, A. S., and Wu, T. L. (2002) Biochem Biophys Res Commun 299, 196-200
10. Dong, X. Y., Rodriguez, C., Guo, P., Sun, X., Talbot, J. T., Zhou, W., Petros, J., Li, Q., Vessella, R. L., Kibel, A. S., Stevens, V. L., Calle, E. E., and Dong, J. T. (2008) Hum Mol Genet 17, 1031-1042
11. Gee, H. E., Buffa, F. M., Camps, C., Ramachandran, A., Leek, R., Taylor, M., Patil, M., Sheldon, H., Betts, G., Homer, J., West, C., Ragoussis, J., and Harris, A. L. (2011) Br J Cancer 104, 1168-1177
12. Williams, G. T., and Farzaneh, F. (2012) Nat Rev Cancer 12, 84-88
13. Runte, M., Huttenhofer, A., Gross, S., Kiefmann, M., Horsthemke, B., and Buiting, K. (2001) Hum Mol Genet 10, 2687-2700
14. Vitali, P., Royo, H., Marty, V., Bortolin-Cavaille, M. L., and Cavaille, J. (2010) J Cell Sci 123, 70-83
15. Cavaille, J., Buiting, K., Kiefmann, M., Lalande, M., Brannan, C. I., Horsthemke, B., Bachellerie, J. P., Brosius, J., and Huttenhofer, A. (2000) Proc Natl Acad Sci USA 97, 14311-14316
16. Stanford, J. L., FitzGerald, L. M., McDonnell, S. K., Carlson, E. E., McIntosh, L. M., Deutsch, K., Hood, L., Ostrander, E. A., and Schaid, D. J. (2009) Hum Mol Genet 18, 1839-1848
17. Gillanders, E. M., Xu, J., Chang, B. L., Lange, E. M., Wiklund, F., Bailey-Wilson, J. E., Baffoe-Bonnie, A., Jones, M., Gildea, D., Riedesel, E., Albertus, J., Isaacs, S. D., Wiley, K. E., Mohai, C. E., Matikainen, M. P., Tammela, T. L., Zheng, S. L., Brown, W. M., Rokman, A., Carpten, J. D., Meyers, D. A., Walsh, P. C., Schleutker, J., Gronberg, H., Cooney, K. A., Isaacs, W. B., and Trent, J. M. (2004) J Natl Cancer Inst 96, 1240-1247
18. Lange, E. M., Ho, L. A., Beebe-Dimmer, J. L., Wang, Y., Gillanders, E. M., Trent, J. M., Lange, L. A., Wood, D. P., and Cooney, K. A. (2006) Hum Genet 119, 400-407
19. Xu, J., Dimitrov, L., Chang, B. L., Adams, T. S., Turner, A. R., Meyers, D. A., Eeles, R. A., Easton, D. F., Foulkes, W. D., Simard, J., Giles, G. G., Hopper, J. L., Mahle, L., Moller, P., Bishop, T., Evans, C., Edwards, S., Meitz, J., Bullock, S., Hope, Q., Hsieh, C. L., Halpern, J., Balise, R. N., Oakley-Girvan, I., Whittemore, A. S., Ewing, C. M., Gielzak, M., Isaacs, S. D., Walsh, P. C., Wiley, K. E., Isaacs, W. B., Thibodeau, S. N., McDonnell, S. K., Cunningham, J. M., Zarfas, K. E., Hebbring, S., Schaid, D. J., Friedrichsen, D. M., Deutsch, K., Kolb, S., Badzioch, M., Jarvik, G. P., Janer, M., Hood, L., Ostrander, E. A., Stanford, J. L., Lange, E. M., Beebe-Dimmer, J. L., Mohai, C. E., Cooney, K. A., Ikonen, T., Baffoe-Bonnie, A., Fredriksson, H., Matikainen, M. P., Tammela, T., Bailey-Wilson, J., Schleutker, J., Maier, C., Herkommer, K., Hoegel, J. J., Vogel, W., Paiss, T., Wiklund, F., Emanuelsson, M., Stenman, E., Jonsson, B. A., Gronberg, H., Camp, N. J., Farnham, J., Cannon-Albright, L. A., and Seminara, D. (2005) Am J Hum Genet 77, 219-229
20. Schwab, M. (1998) Bioessays 20, 473-479

21. Berruti, A., Mosca, A., Tucci, M., Terrone, C., Torta, M., Tarabuzzi, R., Russo, L., Cracco, C., Bollito, E., Scarpa, R. M., Angeli, A., and Dogliotti, L. (2005) Endocr Relat Cancer 12, 109-117
22. Wafa, L. A., Palmer, J., Fazli, L., Hurtado-Coll, A., Bell, R. H., Nelson, C. C., Gleave, M. E., Cox, M. E., and Rennie, P. S. (2007) Hum Pathol 38, 161-170
23. Avgeris, M., Koutalellis, G., Fragoulis, E. G., and Scorilas, A. (2008) Clin Biochem 41, 1140-1149
24. Kaplan-Lefko, P. J., Chen, T. M., Ittmann, M. M., Barrios, R. J., Ayala, G. E., Huss, W. J., Maddison, L. A., Foster, B. A., and Greenberg, N. M. (2003) Prostate 55, 219-237
25. Evangelou, A. I., Winter, S. F., Huss, W. J., Bok, R. A., and Greenberg, N. M. (2004) J Cell Biochem 91, 671-683
26. Sun, Y., Niu, J., and Huang, J. (2009) Am J Transl Res 1, 148-162
27. Kishore, S., Khanna, A., Zhang, Z., Hui, J., Balwierz, P. J., Stefan, M., Beach, C., Nicholls, R. D., Zavolan, M., and Stamm, S. (2010) Hum Mol Genet 19, 1153-1164
28. Nishikura, K. (2010) Annu Rev Biochem 79, 321-349
29. Garrett, S., and Rosenthal, J. J. (2012) Science 335, 848-851
30. Wang, E. T., Sandberg, R., Luo, S., Khrebtukova, I., Zhang, L., Mayr, C., Kingsmore, S. F., Schroth, G. P., and Burge, C. B. (2008) Nature 456, 470-476
31. Lopez, A. J. (1998) Annu Rev Genet 32, 279-305
32. Faustino, N. A., and Cooper, T. A. (2003) Genes Dev 17, 419-437
33. David, C. J., and Manley, J. L. (2010) Genes Dev 24, 2343-2364
34. Schwerk, C., and Schulze-Osthoff, K. (2005) Mol Cell 19, 1-13
35. Werry, T. D., Loiacono, R., Sexton, P. M., and Christopoulos, A. (2008) Pharmacol Ther 119, 7-23
36. Labasque, M., Meffre, J., Carrat, G., Becamel, C., Bockaert, J., and Marin, P. (2010) Mol Pharmacol 78, 818-826
37. Niswender, C. M., Copeland, S. C., Herrick-Davis, K., Emeson, R. B., and Sanders-Bush, E. (1999) J Biol Chem 274, 9472-9478
38. Flomen, R., Knight, J., Sham, P., Kerwin, R., and Makoff, A. (2004) Nucleic Acids Res 32, 2113-2122
39. Werry, T. D., Gregory, K. J., Sexton, P. M., and Christopoulos, A. (2005) J Neurochem 93, 1603-1615
40. Li, L., Xiong, Y., Qu, Y., Mao, M., Mu, W., Wang, H., and Mu, D. (2008) Acta Neuropathol 115, 297-303
41. Maroni, P. D., Koul, S., Meacham, R. B., and Koul, H. K. (2004) Cell Commun Signal 2,
42. Osaki, M., Oshimura, M., and Ito, H. (2004) Apoptosis 9, 667-676
43. Hodge, J. C., Bub, J., Kaul, S., Kajdacsy-Balla, A., and Lindholm, P. F. (2003) Cancer Res 63, 1359-1364
44. Schmidt, L. J., Duncan, K., Yadav, N., Regan, K. M., Verone, A. R., Lohse, C. M., Pop, E. A., Attwood, K., Wilding, G., Mohler, J. L., Sebo, T. J., Tindall, D. J., and Heemers, H. V. (2012) Mol Endocrinol 26, 716-735
45. Zhu, Y., and Parada, L. F. (2002) Nature reviews. Cancer 2, 616-626
46. Pollack, I. F., and Jakacki, R. I. (2011) Nat Rev Neurol 7, 495-506
47. (2012) Brain and Spinal Cord Tumors in Children. American Cancer Society, Atlanta, Ga.
48. Ries, L. A. G., Smith, M. A., Gurney, J. G., Linet, M., Tamra, T., Young, J. L., and Bunin, G. R. (1999) Cancer Incidence and Survival among Children and Adolescents: United States SEER Program 1975-1995, National Cancer Institute, Bethesda, Md.
49. Raymond, J. R., Mukhin, Y. V., Gelasco, A., Turner, J., Collinsworth, G., Gettys, T. W., Grewal, J. S., and Garnovskaya, M. N. (2001) Pharmacology & therapeutics 92, 179-212
50. Merzak, A., Koochekpour, S., Fillion, M. P., Fillion, G., and Pilkington, G. J. (1996) Brain Res Mol Brain Res 41, 1-7
51. Hasselblatt, M., Bohm, C., Tatenhorst, L., Dinh, V., Newrzella, D., Keyvani, K., Jeibmann, A., Buerger, H., Rickert, C. H., and Paulus, W. (2006) The American journal of surgical pathology 30, 66-74
52. Maas, S., Patt, S., Schrey, M., and Rich, A. (2001) Proc Natl Acad Sci USA 98, 14687-14692
53. McGrew, L., Price, R. D., Hackler, E., Chang, M. S., and Sanders-Bush, E. (2004) Mol Pharmacol 65, 252-256
54. Raymond, J. R., Mukhin, Y. V., Gelasco, A., Turner, J., Collinsworth, G., Gettys, T. W., Grewal, J. S., and Garnovskaya, M. N. (2001) Pharmacol Ther 92, 179-212
55. Ji, S. P., Zhang, Y., Van Cleemput, J., Jiang, W., Liao, M., Li, L., Wan, Q., Backstrom, J. R., and Zhang, X. (2006) Nat Med 12, 324-329
56. Li, J., Yen, C., Liaw, D., Podsypanina, K., Bose, S., Wang, S. I., Puc, J., Miliaresis, C., Rodgers, L., McCombie, R., Bigner, S. H., Giovanella, B. C., Ittmann, M., Tycko, B., Hibshoosh, H., Wigler, M. H., and Parsons, R. (1997) Science 275, 1943-1947
57. McCall, P., Witton, C. J., Grimsley, S., Nielsen, K. V., and Edwards, J. (2008) Br J Cancer 99, 1296-1301
58. Marston, O. J., and Heisler, L. K. (2009) Neuropsychopharmacology 34, 252-253
59. Dorsam, R. T., and Gutkind, J. S. (2007) Nat Rev Cancer 7, 79-94
60. Marinissen, M. J., and Gutkind, J. S. (2001) Trends Pharmacol Sci 22, 368-376
61. Julius, D., Livelli, T. J., Jessell, T. M., and Axel, R. (1989) Science 244, 1057-1062
62. Kahan, C., Julius, D., Pouyssegur, J., and Seuwen, K. (1992) Exp Cell Res 200, 523-527
63. Pirozhok, I., Meye, A., Hakenberg, O. W., Fuessel, S., and Wirth, M. P. (2010) Urol Int 84, 452-460
64. Dizeyi, N., Bjartell, A., Nilsson, E., Hansson, J., Gadaleanu, V., Cross, N., and Abrahamsson, P. A. (2004) Prostate 59, 328-336
65. Siddiqui, E. J., Shabbir, M., Mikhailidis, D. P., Thompson, C. S., and Mumtaz, F. H. (2006) J Urol 176, 1648-1653
66. Gurevich, I., Englander, M. T., Adlersberg, M., Siegal, N. B., and Schmauss, C. (2002) J Neurosci 22, 10529-10532
67. Saucier, C., Morris, S. J., and Albert, P. R. (1998) Biochem Pharmacol 56, 1347-1357
68. Bonkhoff, H. (2001) Ann Oncol 12 Suppl 2, S141-144
69. Taplin, M. E., George, D. J., Halabi, S., Sanford, B., Febbo, P. G., Hennessy, K. T., Mihos, C. G., Vogelzang, N. J., Small, E. J., and Kantoff, P. W. (2005) Urology 66, 386-391
70. Ather, M. H., Abbas, F., Faruqui, N., Israr, M., and Pervez, S. (2008) BMC Urol 8, 21
71. Kim, J., Adam, R. M., and Freeman, M. R. (2002) Cancer Res 62, 1549-1554
72. Zhang, X. Q., Kondrikov, D., Yuan, T. C., Lin, F. F., Hansen, J., and Lin, M. F. (2003) Oncogene 22, 6704-6716

73. Bromidge, S. M., Duckworth, M., Forbes, I. T., Ham, P., King, F. D., Thewlis, K. M., Blaney, F. E., Naylor, C. B., Blackburn, T. P., Kennett, G. A., Wood, M. D., and Clarke, S. E. (1997) J Med Chem 40, 3494-3496
74. Higgins, G. A., Ouagazzal, A. M., and Grottick, A. J. (2001) Br J Pharmacol 133, 459-466
75. Schlag, B. D., Lou, Z., Fennell, M., and Dunlop, J. (2004) J Pharmacol Exp Ther 310, 865-870

The foregoing examples are intended to illustrate the invention. Those skilled in the art will recognized that minor modifications can be made without deviating from the spirit of the invention.

We claim:

1. A method comprising testing in vitro a biological sample for the presence of small nucleolar RNA HBII-52, comparing the amount of HBII-52 to the amount of HBII-52 in a non-cancer control, and determining the amount of HBII-52 in the relative to the amount of HBII-52 in the non-cancer control, wherein the sample is a sample of prostate tissue.

2. The method of claim 1, wherein the testing comprises amplification of an HBII-52 sequence using a polymerase chain reaction.

3. The method of claim 2, wherein the polymerase chain reaction comprises amplifying the HBII-52 using a first primer which comprises or consists of SEQ ID NO:3 and a second primer which comprises or consists of SEQ ID NO:4.

4. A method for monitoring an individual undergoing therapy for a disorder associated with small nucleolar RNA (snoRNA) HBII-52 expression comprising obtaining a first sample from the individual and testing it to determine a first amount of HBII-52, treating the individual with a therapeutic agent intended to treat the disorder, obtaining a second biological sample from the individual and testing the second biological sample to determine a second amount of HBII-52.

5. The method of claim 4, wherein a reduction in the amount of the HBII-52 in the second biological sample relative to the amount of HBII-52 in the first biological sample indicates the therapy is effective, and wherein a lack of reduction of the HBII-52 in the second biological sample relative to the amount of the HBII-52 in the first biological sample indicates the therapy is not effective.

6. The method of claim 5, wherein the individual is undergoing therapy for prostate cancer.

7. A method for treating a patient comprising testing a biological sample of prostate tissue for small nucleolar RNA (snoRNA) HBII-52, determining elevated HBII-52 in the biological sample relative to a control, and administering to an individual from which the sample was obtained at least one therapeutic agent effective for treating at least one disorder associated with the elevated HBII-52 in the sample.

8. The method of claim 7, wherein the therapeutic agent specifically disrupts function of HBII-52 and/or decreases HBII-52 in cancer cells, or an antagonist of $5\text{-HT}_{2c}R$.

9. A method for therapy of a subject diagnosed with prostate cancer comprising administering to the subject a composition comprising a therapeutically effective amount of a therapeutic agent which specifically disrupts function of HBII-52 and/or decreases HBII-52 in cancer cells, or is an antagonist of $5\text{-HT}_{2c}R$.

* * * * *